United States Patent [19]

Matsumoto et al.

[11] Patent Number: 4,649,144
[45] Date of Patent: Mar. 10, 1987

[54] ANTIBACTERIAL 7-(3-AMINO-1-PYRROLIDINYL)-1-CYCLO-PROPYL-6-FLUORO-1,4-DIHYDRO-4-OXO-1,8-NAPHTHYRIDINE-3-CARBOXYLIC ACID DERIVATIVES

[75] Inventors: Jun-ichi Matsumoto, Ikoma; Teruyuki Miyamoto, Sakai; Hitoshi Uno; Shinichi Nakamura, both of Takatsuki, all of Japan

[73] Assignee: Dainippon Pharmaceutical Co., Ltd., Osaka, Japan

[21] Appl. No.: 632,853

[22] Filed: Jul. 20, 1984

[30] Foreign Application Priority Data

Jul. 27, 1983 [JP] Japan ................................. 58-138000
Jun. 6, 1984 [JP] Japan ................................. 59-117266

[51] Int. Cl.$^4$ .................. A61K 31/435; C07D 471/04
[52] U.S. Cl. ..................................... 514/300; 546/123
[58] Field of Search .......................... 546/123; 514/300

[56] References Cited

U.S. PATENT DOCUMENTS 4,248,629  8/1981  Grohe et al. ................. 514/300
4,341,784  7/1982  Matsumoto et al. ........... 514/300
4,359,578  11/1982 Matsumoto et al. ........... 544/362
4,382,937  5/1983  Matsumoto et al. ........... 546/123

FOREIGN PATENT DOCUMENTS 49355     4/1982  European Pat. Off. ........... 546/123
0106489   4/1984  European Pat. Off. ........... 546/123
57/106681 7/1982  Japan ......................... 544/362

OTHER PUBLICATIONS

"Organic Chemistry", Morrison & Boyd, 2nd Ed., Chapter 27, 1960.

Primary Examiner—Richard A. Schwartz
Assistant Examiner—Kurt G. Briscoe
Attorney, Agent, or Firm—Wenderoth, Lind and Ponack

[57] ABSTRACT

The present invention relates to a 1,8-naphthyridine derivative of the formula

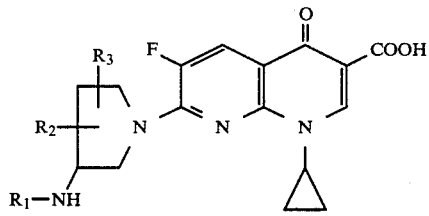

wherein $R_1$, $R_2$ and $R_3$ are the same or different and each hydrogen or lower alkyl having 1 to 5 carbon atoms; and esters thereof and salts thereof and processes for preparation thereof. These compounds show excellent antibacterial activity and are useful antibacterial agents.

15 Claims, No Drawings

ANTIBACTERIAL 7-(3-AMINO-1-PYRROLIDINYL)-1-CYCLOPROPYL-6-FLUORO-1,4-DIHYDRO-4-OXO-1,8-NAPHTHYRIDINE-3-CARBOXYLIC ACID DERIVATIVES

This invention relates to novel 1,8-naphthyridine compounds having extremely high antibacterial activities and processes for preparing said novel compounds.

The compounds of the invention are 1,8-naphthyridine derivatives represented by the formula

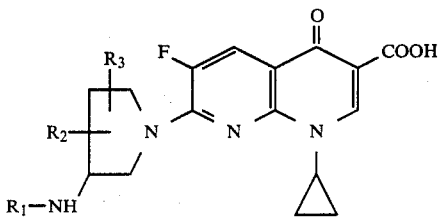

wherein $R_1$, $R_2$ and $R_3$, which may be the same or different, are each hydrogen or alkyl having 1 to 5 carbon atoms; and esters and pharmaceutically acceptable salts thereof.

The salts of the compounds of the formula (I) or their esters may be any salt formed from the compounds of formula (I) or their esters with pharmaceutically acceptable acids or bases. The salts of the compounds of the invention are the salts derived from organic acids such as acetic acid, lactic acid, succinic acid, methanesulfonic acid, maleic acid, malonic acid, or gluconic acid; those from amino acids such as aspartic acid or glutamic acid; those from inorganic acids such as hydrochloric acid or phosphoric acid; metal (e.g. sodium, potassium, zinc, silver, etc.) salts; or organic base salts.

The esters of the compounds of formula (I) include not only the substituted or unsubstituted aliphatic esters, especially the lower alkyl esters having 1 to 5 carbon atoms such as methyl or ethyl ester, but also esters that can be easily converted to the compounds (I) by hydrolysis or by enzymatic hydrolysis in vivo, such as pivaloyloxymethyl ester, ethoxycarbonyloxyethyl ester, aminoethyl esters (e.g., dimethylaminoethyl ester, 1-piperidinylethyl ester, etc.), 5-indanyl ester, phthalidyl ester, or hydroxyalkyl esters (e.g. 2-hydroxyethyl ester, 2,3-dihydroxypropyl ester, etc.).

The compounds of the invention may also exist as hydrates. Hence, these hydrates are also included in the compounds of the present invention.

The compounds of formula (I) and the esters and salts thereof will therefore all be generically referred to herein as the compounds of this invention.

The compounds of the invention have at least one asymmetric carbon atom on its pyrrolidine ring and therefore exist in optically active forms. The D isomer, L isomer as well as mixtures thereof, including the racemic mixture, are all included in this invention.

The compounds of the invention also include those having two asymmetric carbon atoms on the pyrrolidine ring, and therefore such compounds of the invention can exist as stereoisomers having a different configuration. These stereoisomers are also included in the compounds of this invention.

BACKGROUND OF THE INVENTION

U.S. Pat. No. 4,341,784 issued on July 27, 1982 discloses the following compounds with antibacterial activity.

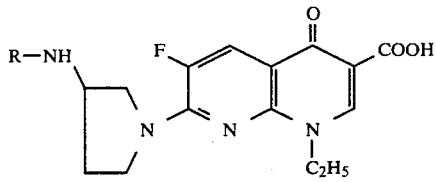

wherein R is methyl, ethyl or propyl.

But the compounds of this invention are surprisingly superior to the above known compounds in their antibacterial activity as shown hereinafter.

On the other hand, U.S. Pat. No. 4,382,937 issued on May 10, 1983 discloses that compounds in which the ethyl group of the 1-position of 1,8-naphthyridine of the foregoing formula has been converted to the vinyl group have antibacterial activity.

European Laid-Open Patent Specification No. 49355 published on Apr. 4, 1982 discloses the following general formula

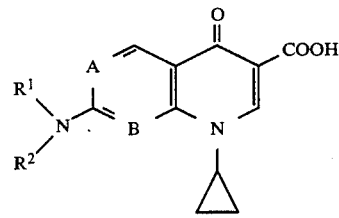

In regard to the group

shown in this formula, there is however no disclosure at all as to whether this is an amino-substituted pyrrolidinyl group and an amino and alkyl-substituted pyrrolidinyl group.

It is an object of the invention to provide novel 1,8-naphthyridine compounds (I) having high antibacterial activities against both Gram-positive bacteria and Gram-negative bacteria, as well as esters and pharmaceutically acceptable salts thereof, and processes for preparing these novel compounds.

Another object of the invention is to provide a pharmaceutical composition which contains an antibacterially effective amount of a compound selected from compounds having the structural formula (I), esters and pharmaceutically acceptable salts thereof.

The invention further provides a method for treating bacterial infectious diseases which comprises administering to warm-blooded animals an antibacterially effective amount of the compound of this invention or the aforesaid pharmaceutical composition.

These and other objects of the invention will become apparent from the following description.

The compounds of the invention represented by formula (I) include as preferred compounds the following.

7-(3-Amino-1-pyrrolidinyl)-1-cyclopropyl-6-fluoro-1,4-dihydro-4-oxo-1,8-naphthyridine-3-carboxylic acid (hereinafter referred to as compound 1),

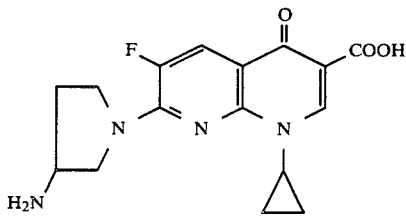

1-Cyclopropyl-6-fluoro-7-(3-methylamino-1-pyrrolidinyl)-1,4-dihydro-4-oxo-1,8-naphthyridine-3-carboxylic acid (hereinafter referred to as compound 2),

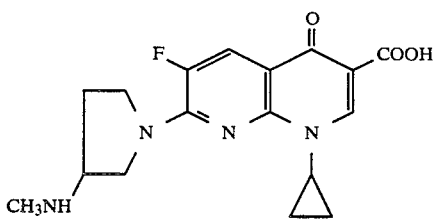

1-Cyclopropyl-7-(3-ethylamino-1-pyrrolidinyl)-6-fluoro-1,4-dihydro-4-oxo-1,8-naphthyridine-3-carboxylic acid,

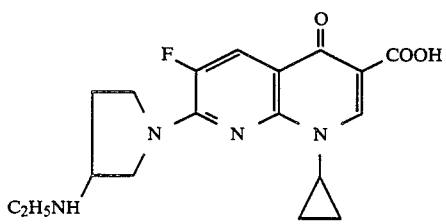

7-(3-Amino-2-methyl-1-pyrrolidinyl)-1-cyclopropyl-6-fluoro-1,4-dihydro-4-oxo-1,8-naphthyridine-3-carboxylic acid.

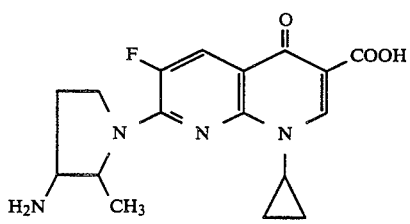

7-(3-Amino-4-methyl-1-pyrrolidinyl)-1-cyclopropyl-6-fluoro-1,4-dihydro-4-oxo-1,8-naphthyridine-3-carboxylic acid (hereinafter referred to as compound 3),

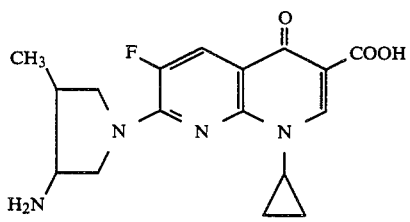

7-(3-Amino-3-methyl-1-pyrrolidinyl)-1-cyclopropyl-6-fluoro-1,4-dihydro-4-oxo-1,8-naphthyridine-3-carboxylic acid (hereinafter referred to as compound 4),

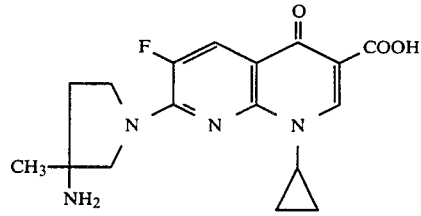

7-(3-Amino-4-ethyl-1-pyrrolidinyl)-1-cyclopropyl-6-fluoro-1,4-dihydro-4-oxo-1,8-naphthyridine-3-carboxylic acid,

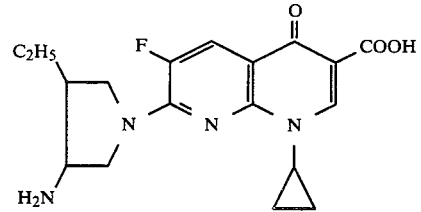

7-(4-Amino-2-methyl-1-pyrrolidinyl)-1-cyclopropyl-6-fluoro-1,4-dihydro-4-oxo-1,8-naphthyridine-3-carboxylic acid,

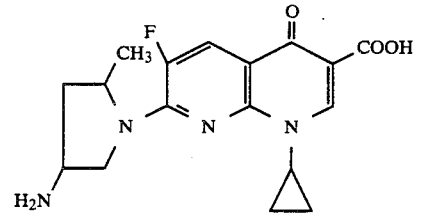

7-(3-Amino-4,4-dimethyl-1-pyrrolidinyl)-1-cyclopropyl-6-fluoro-1,4-dihydro-4-oxo-1,8-naphthyridine-3-carboxylic acid,

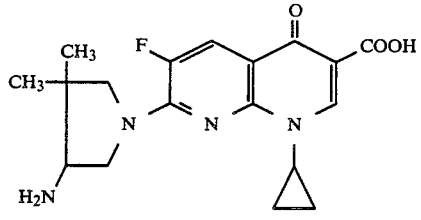

1-cyclopropyl-6-fluoro-7-(3-methyl-4-methylamino-1-pyrrolidinyl)-1,4-dihydro-4-oxo-1,8-naphthyridine-3-carboxylic acid,

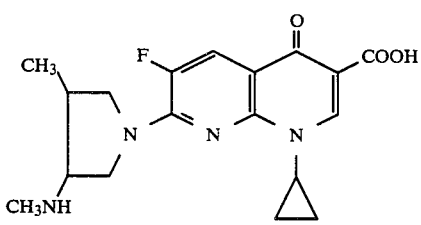

The lower alkyl esters having 1 to 5 carbon atoms of the above compounds and the pharmaceutically acceptable acid addition salts of these compounds, such as the hydrochlorides and methanesulfonates, are also suitable.

Of these compounds, especially to be preferred are the following:

7-(3-Amino-1-pyrrolidinyl)-1-cyclopropyl-6-fluoro-1,4-dihydro-4-oxo-1,8-naphthyridine-3-carboxylic acid (Compound 1), 1-Cyclopropyl-6-fluoro-7-(3-methylamino-1-pyrrolidinyl)-1,4-dihydro-4-oxo-1,8-naphthyridine-3-carboxylic acid (Compound 2), 7-(3-Amino-4-methyl-1-pyrrolidinyl)-1-cyclopropyl-6-fluoro-1,4-dihydro-4-oxo-1,8-naphthyridine-3-carboxylic acid (Compound 3), 7-(3-Amino-3-methyl-1-pyrrolidinyl)-1-cyclopropyl-6-fluoro-1,4-dihydro-4-oxo-1,8-naphthyridine-3-carboxylic acid (Compound 4), and the hydrochlorides and the lower alkyl esters having 1 to 3 carbon atoms of the above compounds.

The processes for preparing the compounds of this invention will now be described.

As principal methods for preparing the compounds of this invention, the following processes A, B, C and D can be named. These processes will be shown by their reaction schemes.

A. Displacement by pyrrolidine derivatives (Reaction A)

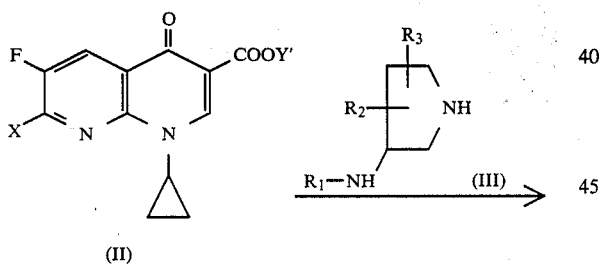

wherein:

X is a reactive group replaceable by a nitrogen atom in a pyrrolidine ring having a hydrogen at position 1 of that ring, and Y' is hydrogen or an aliphatic group.

B. Process via the Dieckmann reaction (Reaction B)

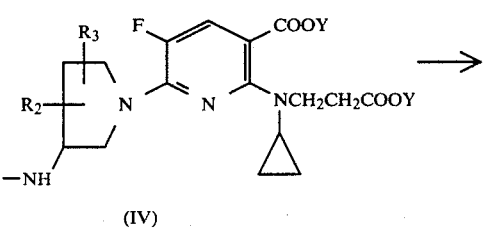

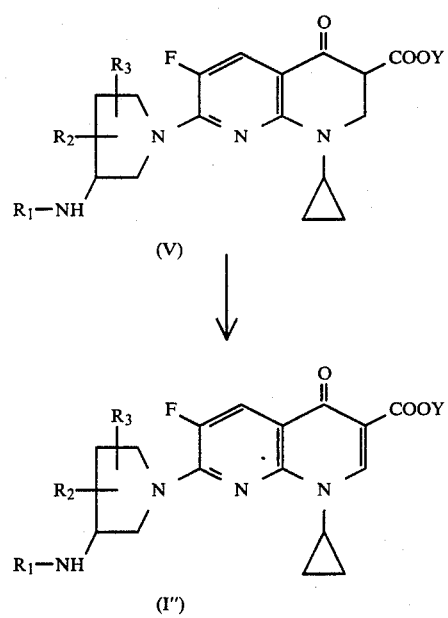

C. Cyclization of β-aminoacrylates (Reaction C)

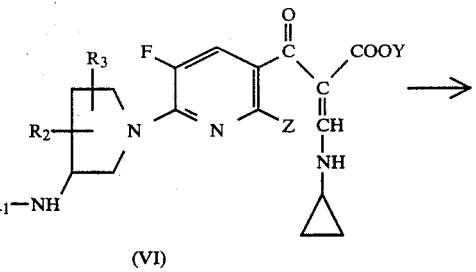

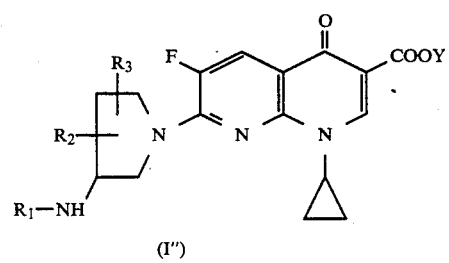

wherein Z is halogen.

D. Hydrolysis (Reaction D)

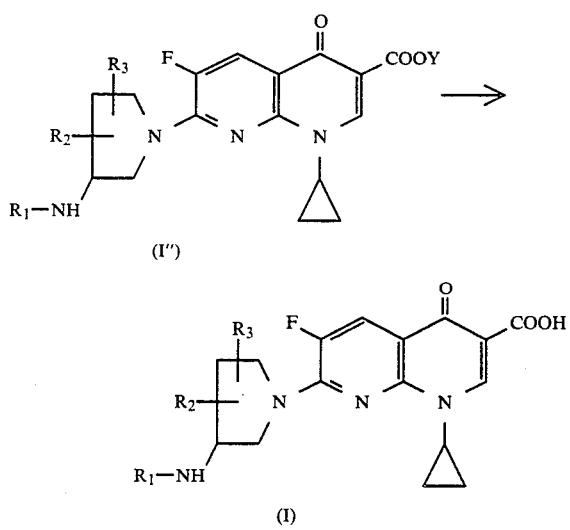

(I'')

(I)

In the foregoing reaction schemes A, B, C and D, the groups $R_1$, $R_2$ and $R_3$ may be the same or different, and each represents hydrogen or lower alkyl having 1 to 5 carbon atoms, and Y represents a substituted or unsubstituted aliphatic group, preferably a lower alkyl group having 1 to 5 carbon atoms.

These reactions A, B, C and D will now be more fully described.

Process A: Displacement by pyrrolidine derivatives
(Reaction A)

The compounds of this invention can be prepared by reacting a carboxylic acid of the formula

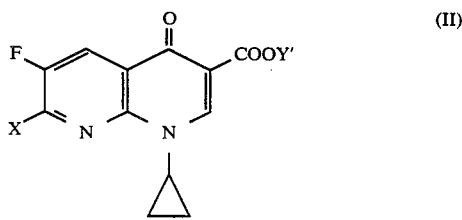

wherein X is a reactive group replaceable by a nitrogen atom in a pyrrolidine ring having a hydrogen at position 1 of that ring, and Y' is hydrogen or an aliphatic group, or its ester, preferably a lower alkyl ester having 1 to 5 carbon atoms, with a pyrrolidine derivative of the formula

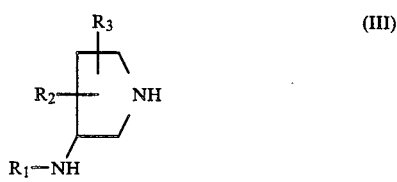

wherein $R_1$, $R_2$, and $R_3$ are as defined hereinbefore.

The reactive functional groups shown by X in the formula (II) are arylsulfonyl, lower alkylsulfonyl having 1 to 5 carbon atoms, halogen, lower alkoxy having 1 to 5 carbon atoms, lower alkylthio having 1 to 5 carbon atoms, lower alkylsulfinyl having 1 to 5 carbon atoms, arylsulfonyloxy, lower alkylsulfonyloxy having 1 to 5 carbon atoms, or the like, of which especially preferred are toluenesulfinyl, toluenesulfonyl and halogen.

The reaction of the compound (II) with the compound (III) is carried out in an inert solvent that can at least partially dissolve these compounds, at 20°–180° C., preferably at 30°–150° C., for 5–120 minutes, usually for 20–60 minutes, with stirring.

The solvent used in this reaction should be selected according to the properties of the starting materials to be used. Examples of the inert solvent are aliphatic alcohols such as ethanol or propanol, aromatic hydrocarbons such as benzene or toluene, haloalkanes such as dichloroethane or chloroform, ethers such as tetrahydrofuran, dioxane or diphenyl ether, acetonitrile, dimethyl sulfoxide and dimethylformamide. They may be used either alone or in combination with each other.

The solvents mentioned above can be used also in the processes B, C and D later described, if required.

The compound (III) is used in the amount equivalent to or slightly in excess of the compound (II). Depending upon the type of the functional group X in the compound (II), the reaction results in producing an acid such as hydrochloric acid as a by-product. In such a case the reactin is generally carried out in the presence of an acid acceptor, but the compound (III) may be used in excess to make itself serve as an acid acceptor. Examples of the acid acceptor is a base such as sodium bicarbonate, sodium carbonate, potassium carbonate, triethylamine, pyridine or picoline.

In this reaction the compound (III) in which the amine substituent is protected by a protecting group commonly used in the chemistry of β-lactam antibiotics, peptides, or nucleic acids may be used and afterwards the protecting group of the reaction product be removed in the usual manner. As the protecting group, any may be used so long as it is one that can be removed without damaging the structure of the compounds of this invention formed by the reaction A.

Specific examples of the protective group include acyl groups such as formyl, acetyl or trifluoroacetyl; substituted or unsubstituted alkoxycarbonyl groups such as ethoxycarbonyl, β-iodoethoxycarbonyl, β,β,β-trichloroethoxycarbonyl, t-butoxycarbonyl, β-(p-toluenesulfonyl)-ethoxycarbonyl, benzyloxycarbonyl or p-methoxybenzyloxycarbonyl; vinyloxycarbonyl; methyl groups substituted by phenyl or benzyloxy such as benzyl, trityl or benzyloxymethyl; alkylsilyl groups such as trimethylsilyl or t-butyldimethylsilyl; arylsulfonyl groups such as p-toluenesulfonyl; o-nitrophenylsulfenyl; tetrahydropyranyl; diphenylphosphinyl.

The starting compounds (II) are prepared in accordance with the methods described in the hereinafter-given Reference Examples 1, 10 and 11. The starting compounds (III), which are new, are prepared in accordance with the methods described in Reference Examples 2 to 9.

Process B: Process via the Dieckmann reaction
(Reaction B)

The esters of the compounds (I) in the invention are also prepared by cyclizing a pyridine derivative of the formula

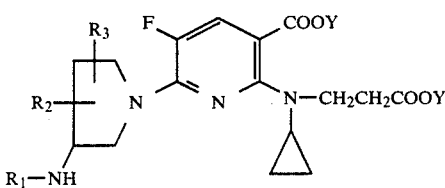

(IV)

in which Y is the same or different aliphatic group, and $R_1$, and $R_2$ and $R_3$ are as defined above, in the presence of a base commonly used in the Dieckmann reaction to produce a compound of the formula

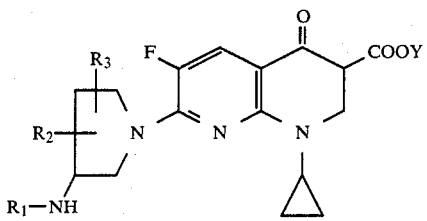

(V)

in which $R_1$, $R_2$, $R_3$ and Y are as defined above, and thereafter dehydrogenating the compound (V).

In the preparation of the compound (V), the starting compound (IV) is cyclized intramolecularly in a solvent in the presence of a base such as metallic sodium, sodium hydride, sodium ethoxide or potassium tert.-butoxide to give the compound (V). The reaction proceeds more effectively by the addition of a small amount of alcohol such as methanol, ethanol, tert.-butyl alcohol, or the like. The preferred solvents for this reaction are aromatic hydrocarbons such as benzene or toluene; ethers such as dioxane, tetrahydrofuran, 1,2-dimethoxyethane or diethylene glycol dimethyl ether; and alcohols such as tert.-butyl alcohol. While there is imposed to particular restriction as to the reaction temperature, usually preferred is a temperature ranging from 10° to 180° C.

In order to dehydrogenate the compound (V), it is allowed to react for a short period of time with a commonly used dehydrogenating reagent such as 2,3-dichloro-5,6-dicyano-1,4-benzoquinone (DDQ), tetrachloro-1,4-benzoquinone (chloranil), tetracyanoethylene, palladium-carbon, bromine, N-bromosuccinimide (NBS), manganese, dioxide, or selenium dioxide in an inert solvent (e.g. aromatic hydrocarbons such as benzene, toluene or xylene, ethyl acetate, ethers such as dioxane, aliphatic alcohols such as ethanol or tert.-butyl alcohol, dimethylformamide, etc.) at about 20° to 200° C. Alternatively, it is also possible to dehydrogenate the compound (V) by heating directly it at above its melting point or just heating it at 50° to 250° C. in an inert solvent such as aroamtic hydrocarbons such as benzene or toluene, aliphatic alcohols such as ethanol, aliphatic hydrocarbons such as n-hexane, haloalkanes such as carbon tetrachloride, dimethylformamide, ethers such as dioxane or diphenyl ether, or the like.

In this reaction it is preferred that the compound (IV) used in the first stage of the reaction has its amine substituent of the pyrrolidine moiety protected with a protecting group as described in the aforementioned process A, and then the protecting group of the product be removed in the usual manner after completion of the reaction.

The starting compounds (IV) are prepared in accordance with the method described in Reference Example 12.

Process C: Cyclization of β-aminoacrylates (Reaction C)

The esters of the compounds (I) in the invention are also prepared by cyclizing a β-aminoacrylate of the formula

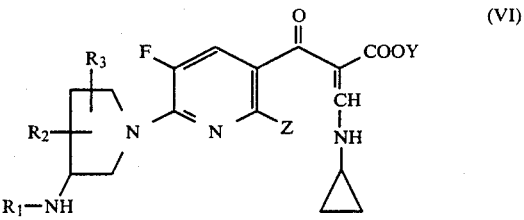

(VI)

in which Z is halogen and $R_1$, $R_2$, $R_3$ and Y are as defined above, in the presence of a base.

This reaction is performed by intramolecularly cyclizing the compound (VI) in an inert solvent such as aliphatic alcohols such as ethanol, isopropyl alcohol or tert.-butyl alcohol, ethers such as dioxane, dimethylformamide, dimethyl sulfoxide, N-methylpyrrolidone, etc. in the presence of a base (e.g. metal hydroxides such as sodium or potassium hydroxide, metal carbonates such as sodium or potassium carbonate, metal bicarbonates such as sodium or potassium bicarbonate, sodium hydride, sodium ethoxide, potassium tert.-butoxide, butyl lithium, triethylamine, 1,8-diazabicyclo[5.4.0]undecene-7 (DBU), or the like). The reaction temperature is usually in the range of from −20° C. to 150° C., preferably from −10° C. to 100° C.

It is preferred that the compound (VI) used in this reaction C be used in the form in which the amine substituent of the pyrrolidine ring is protected as described in the aforesaid reaction B and then the protecting group of the product be removed in the usual manner after completion of the reaction.

The starting compounds (VI) are prepared in accordance with the method described in Reference Example 13.

The esters of the compounds (I) prepared by the Processes A, B and C, as mentioned above, can be converted to the compounds (I) (carboxylic acids) by hydrolysis in accordance with reaction D described below. The compounds (I), if necessary, may be esterified by a conventional method to give the esters of the compounds (I).

D: Hydrolysis (Reaction D)

In forming the compounds (I) by hydrolyzing the esters of compounds (I), this can be achieved by contacting the esters with water. It is generally carried out in the presence of an acid or a base to accelerate and complete the reaction. Examples of suitable acids are the inorganic acids such as hydrochloric acid, hydrobromic acid, hydroiodic acid, sulfuric acid and phosphoric acid, and the organic acids such as acetic acid, oxalic acid and toluenesulfonic acid. Examples of suitable bases are the metal hydroxides such as sodium or barium hydroxide, metal carbonates such as sodium or potassium carbonate, and sodium acetate. The hydrolysis is generally carried out in water, but it may be carried out in an aqueous solvent (e.g. ethanol, dioxane, ethyleneglycol dimethyl ether, benzene, pyridine, acetic acid, etc.). The reaction temperature is preferably one in the range of 20° to 150° C.

The pharmaceutically acceptable salts of the compound (I) or its ester are prepared by treating the compound (I) or its ester with an acid, or the compound (I) with a base or a metal salt. Examples of suitable acids are hydrochloric acid, phosphoric acid, acetic acid, lactic acid, succinic acid, methanesulfonic acid, maleic acid, malonic acid, gluconic acid, aspartic acid and glutamic acid. Examples of suitable bases or metal salts are metal hydroxides such as sodium or potassium hydroxide, metal carbonates such as sodium or potassium carbonate, zinc chloride, zinc sulfate, zinc nitrate and silver nitrate.

The compounds of the invention thus prepared are isolated and purified in a conventional manner. Depending upon the conditions of isolation and/or purification, the compounds are obtained in a form of salt, free carboxylic acid or free amine. These compounds can however be transformed from one form to another to meet the purpose for which they are to be used. Thus, the compounds of this invention are prepared into a form that meets their intended use.

As mentioned hereinabove, there are some compounds of the invention that exist as stereoisomers having a different configuration. These stereoisomaers (cis and trans forms) can be isolated by a conventional method such as fractional crystallization or chromatography. Again, by using the compounds (III) of cis or trans forms as the starting material and submitting them to the reaction of process A of this invention, it is possible to obtain the compounds of this invention having the corresponding configurations. There are practically no difference in the antibacterial activities between these stereoisomers.

The compounds of the invention can also exist in optically active forms which may be obtained separately by the optical resolution procedure known in the art.

The compounds (I), their esters and their salts thus obtained are all new. Especially, the compounds (I) have excellent antibacterial activity and therefore are valuable as antibacterial agents. The compounds (I) and their salts can be used not only as medicines for man and animals, but as fish medicines, agricultural drugs and food preservatives. On the other hand, the esters of the compounds (I) are useful as starting material for preparation of the compounds (I). They are also useful as antibacterial agents, because they themselves have high antibacterial activity and, in the case the ester is easily transformed to the compound (I) in vivo, it shows the same antibacterial effect as the compound (I).

The dosage of the compounds of the invention in administration to man should be adjusted according to the age, body weight, symptoms, the administration route, the number of administration, etc. It is recommended that the compound be administered at a dosage of 5 mg to 5 g per day once or several times daily. The compound may be administered orally or parenterally.

The compounds of the invention may be administered in its as-obtained powder form, but it is usually administered in the form of a pharmaceutical preparation together with the pharmaceutically acceptable adjuvants. Specific examples are tablets, capsules, granules, fine granules, powders, syrups, injections, etc. These pharmaceutical preparations are prepared in a customary manner. Adjuvants for oral administrations are those that are commonly used in the field of pharmaceutical preparations and do not react with the compounds of the invention, such as starch, mannite, crystalline cellulose, CMC Na, etc. Adjuvants for injections are those commonly used in the field of injection such as water, isotonic sodium chloride solution, glucose solution, transfusion solution, etc. When the compound of this invention is to be used as an injection, it can be used for all of such injections as intravenous, intramuscular and subcutaneous injections.

The following Examples 1 to 16 and Reference Examples 1 to 13 will serve to illustrate the processes for preparing the compounds of the present invention.

REFERENCE EXAMPLE 1

Preparation of a starting compound of formula (II) for use in reaction A

Ethyl 7-(p-tolylsulfonyl)-1-cyclopropyl-6-fluoro-1,4-dihydro-4-oxo-1,8-naphthyridine-3-carboxylate

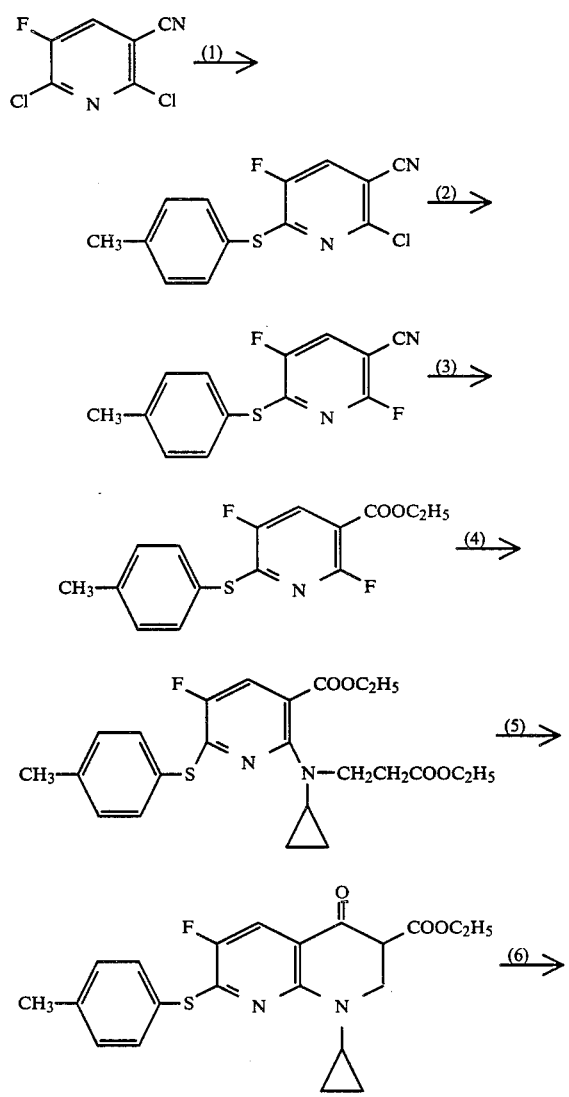

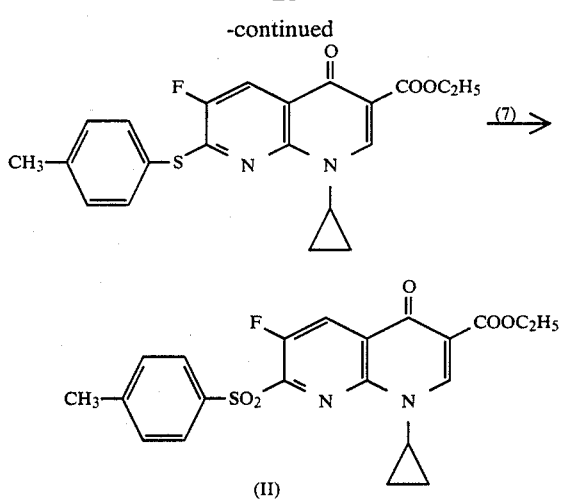

The numbers of the reaction steps described below correspond to the numbers in the above scheme.

(1) 2,6-Dichloro-5-fluoronicotinonitrile (32.5 g) in ethanol (400 ml) was treated at room temperature with potassium salt of p-thiocresol, prepared from p-thiocresol (23.2 g) and potassium hydroxide (12.2 g), to give 2-chloro-6-(p-tolylthio)-5-fluoronicotinonitrile (42.4 g), m.p. 124°–125° C.

(2) To a solution of the above compound (36 g) in dry dimethyl sulfoxide (180 ml) was added anhydrous potassium fluoride (22.2 g), and the mixture was heated at 130°–135° C. for 1 hour with stirring. The solvent was evaporated under reduced pressure and water was added to the residue. The resulting crude crystals were recrystallized from ethanol to give 2,5-difluoro-6-(p-tolylthio)nicotinonitrile (30 g), m.p. 120°–121° C.

(3) The above compound (4 g) in absolute ethanol was treated with dry hydrogen chloride to yield ethyl 2,5-difluoro-6-(p-tolylthio)nicotinate (3 g).

(4) Ethyl 2,5-difluoro-6-(p-tolylthio)nicotinate (25 g) prepared as above was dissolved in dimethylformamide (400 ml). To this solution were added ethyl N-cyclopropylaminopropionate (25.4 g) and sodium bicarbonate (14 g), and the mixture was heated at 100°–110° C. for 10 hours with stirring. The solvent was evaporated under reduced pressure, water was added to the residue, and the mixture was extracted with toluene. The extracts were washed with dilute hydrochloric acid and then with water, and dried over anhydrous sodium sulfate. After evaporation of toluene under reduced pressure, ethyl 6-(p-tolylthio)-2-[N-cyclopropyl-N-(2-ethoxycarbonylethyl)amino]-5-fluoronicotinate (32 g) was obtained as a viscous oil.

(5) To a solution of the above compound (3.2 g) in dry toluene (50 ml) was added 65% sodium hydride (0.32 g) at room temperature and the mixture was stirred for 10 minutes. Catalytic amount of absolute ethanol was added to the mixture and stirring was continued at room temperature for 2 hours followed by heating the mixture at 50°–60° C. for 1 hour. After addition of water, the mixture was neutralized with 10% aqueous acetic acid. The organic layer was separated, dried over anhydrous sodium sulfate, and toluene was evaporated under reduced pressure. The resulting crude crystals were recrystallized from n-hexane-isopropyl ether to give ethyl 7-(p-tolylthio)-1-cyclopropyl-6-fluoro-1,2,3,4-tetrahydro-4-oxo-1,8-naphthyridine-3-carboxylate (2.5 g), m.p. 124°–125° C.

(6) To a solution of the above compound (2.0 g) in toluene (50 ml) was added 2,3-dichloro-5,6-dicyano-p-benzoquinone (1.25 g), and the mixture was stirred at room temperature for 2 hours and then at 50°–60° C. for 1 hour. After cooling, the resulting crystals were filtered and dissolved in chloroform. The solution was washed with 1N sodium hydroxide and with water, and dried over anhydrous sodium sulfate. Chloroform was evaporated and the resulting crude crystals were recrystallized from ethanol-isopropyl ether to give ethyl 7-(p-tolylthio)-1-cyclopropyl-6-fluoro-1,4-dihydro-4-oxo-1,8-naphthyridine-3-carboxylate (1.7 g), m.p. 186°–187° C.

(7) The above compound (1.59 g) and m-chloroperbenzoic acid (80%) (1.90 g) were dissolved in chloroform (50 ml) and the solution was refluxed for 30 minutes. After cooling, the solution was washed with 2N sodium carbonate and then with water and dried over anhydrous sodium sulfate. Chloroform was evaporated and the resulting crude crystals were recrystallized from ethyl acetate to give ethyl 7-(p-tolylsulfonyl)-1-cyclopropyl-6-fluoro-1,4-dihydro-4-oxo-1,8-naphthyridine-3-carboxylate (1.55 g), m.p. 216°–218° C.

The starting materials (II) which have any substituents (—COOY') at the 3-position of their naphthyridine ring other than —COOC$_2$H$_5$ can also be prepared in the same manner as described above.

EXAMPLE 1

Preparation of 7-(3-amino-1-pyrrolidinyl)-1-cyclopropyl-6-fluoro-1,4-dihydro-4-oxo-1,8-naphthyridine-3-carboxylic acid (by the substitution reaction A)

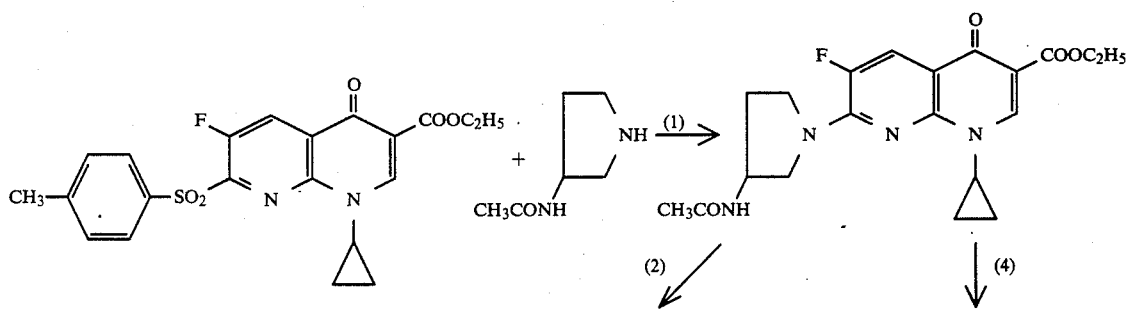

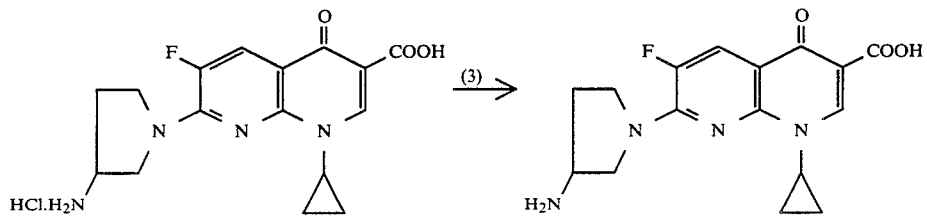

The numbers of the reaction steps described below correspond to the numbers in the above scheme.

(1) A mixture of ethyl 7-(p-tolylsulfonyl)-1-cyclopropyl-6-fluoro-1,4-dihydro-4-oxo-1,8-naphthyridine-3-carboxylate (800 mg), 3-acetylaminopyrrolidine (300 mg), triethylamine (236 mg), and ethanol (25 ml) was refluxed for 2 hours. After evaporation of the solvent under reduced pressure, the residual crude crystals were recrystallized from ethanol-isopropyl ether to give ethyl 7-(3-acetylamino-1-pyrrolidinyl)-1-cyclopropyl-6-fluoro-1,4-dihydro-4-oxo-1,8-naphthyridine-3-carboxylate (600 mg), m.p. 246°–248° C.

(2) A mixture of the compound (600 mg) prepared in (1) and 20% hydrochloric acid (10 ml) was refluxed for 10 hours. The solvent was evaporated under reduced pressure and ethanol was added to the residue. The resulting crystals were filtered to give 7-(3-amino-1-pyrrolidinyl)-1-cyclopropyl-6-fluoro-1,4-dihydro-4-oxo-1,8-naphthyridine-3-carboxylic acid hydrochloride (460 mg), m.p. 275°–280° C. (decompn.), recrystallized from water-ethanol.

(3) The above hydrochloride (370 mg) was dissolved in water (10 ml). To the mixture was added anhydrous sodium acetate (870 mg), and the resulting crystals were filtered, washed with water and then with ethanol, after which they were dried at about 110° C. to give 7-(3-amino-1-pyrrolidinyl)-1-cyclopropyl-6-fluoro-1,4-dihydro-4-oxo-1,8-naphthyridine-3-carboxylic acid (320 mg), m.p. 266°–267° C. (decompn.).

(4) A mixture of the ester (402 mg) obtained in (1) and 10% sodium hydroxide solution (10 ml) was heated at 90°–110° C. for 2 hours with stirring. After neutralization with aqueous acetic acid, the resulting crystals were filtered. The crystals were dissolved in 1N hydrochloric acid (10 ml), the solution was treated with activated carbon and adjusted at pH 7–8 with 1N sodium hydroxide solution. The resulting crystals were filtered, washed with water and then with ethanol, after which they were dried at about 110° C. to give 7-(3-amino-1-pyrrolidinyl)-1-cyclopropyl-6-fluoro-1,4-dihydro-4-oxo-1,8-naphthyridine-3-carboxylic acid (272 g), m.p. 266°–267° C. (decompn.).

REFERENCE EXAMPLE 2

Preparation of starting compound of formula (III)

3-(N-Acetyl-N-methylamino)pyrrolidine

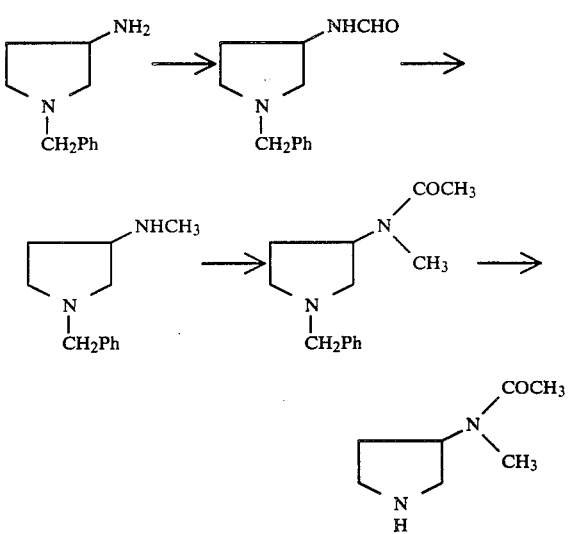

3-Amino-1-benzylpyrrolidine [J. Med. Chem., 11, 1034 (1968)] was allowed to react with formic acid and formamide to give 1-benzyl-3-formylaminopyrrolidine. This compound was reduced with sodium bis(2-methoxyethoxy)-aluminium hydride to give 1-benzyl-3-methylaminopyrrolidine, b.p. 134°–136° C./5–6 mmHg. This compound was treated with acetic anhydride to give 3-(N-acetyl-N-methylamino)-1-benzylpyrrolidine, b.p. 144°–147° C./0.5 mmHg. This compound was hydrogenated catalytically in the presence of 5% palladium-carbon to give 3-(N-acetyl-N-methylamino)-pyrrolidine as an oil.

EXAMPLE 2

Preparation of 1-cyclopropyl-6-fluoro-7-(3-methylamino-1-pyrrolidinyl)-1,4-dihydro-4-oxo-1,8-naphthyridine-3-carboxylic acid (by the substitution reaction A)

Reference Example 3

Preparation of a starting compound of formula (III) 3-(N-Acetyl-N-n-propylamino)pyrrolidine

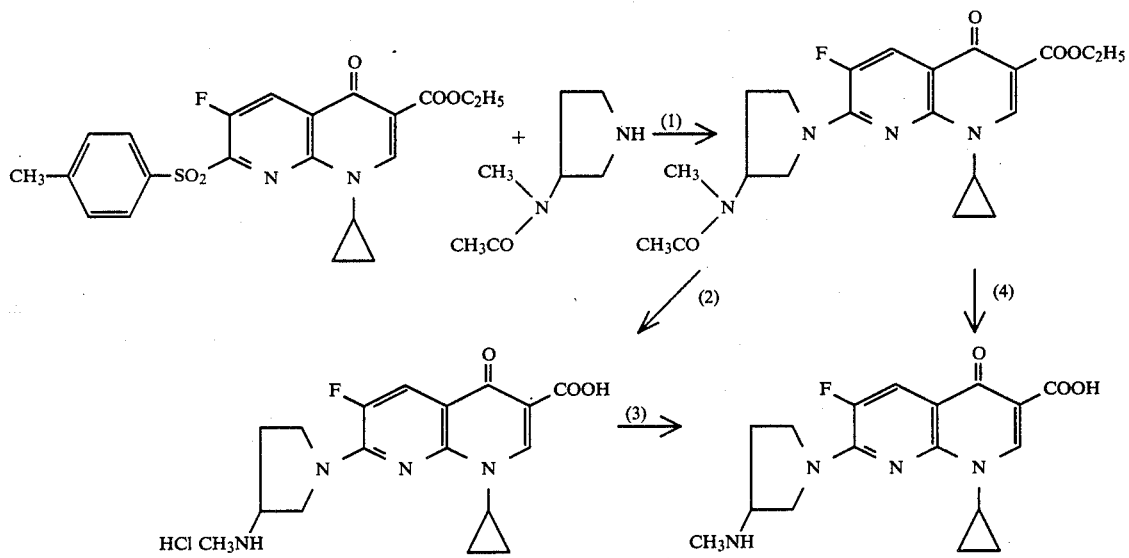

The numbers of the reaction steps described below correspond to the numbers in the above scheme.

(1) A mixture of ethyl 7-(p-tolylsulfonyl)-1-cyclopropyl-6-fluoro-1,4-dihydro-4-oxo-1,8-naphthyridine-3-carboxylate (1.72 g), N-acetyl-N-methylaminopyrrolidine (740 mg), triethylamine (522 mg), and acetonitrile (40 ml) was refluxed for 1.5 hours. After evaporation of the solvent under reduced pressure, ethanol was added to the residue, and after cooling, the resulting crystals were filtered to give ethyl 1-cyclopropyl-6-fluoro-7-[3-(N-acetylmethylamino)-1-pyrrolidinyl]-1,4-dihydro-4-oxo-1,8-naphthyridine-3-carboxylate (1.44 g), m.p. 203°–204° C., recrystallized from ethanol.

(2) The above ester (1.34 g) was treated in the same manner as described in Example 1-(2) to give 1-cyclopropyl-6-fluoro-7-(3-methylamino-1-pyrrolidinyl)-1,4-dihydro-4-oxo-1,8-naphthyridine-3-carboxylic acid hydrochloride (900 mg), m.p. 284°–289° C. (decompn.), recrystallized from water-ethanol.

(3) The above hydrochloride (900 mg) was treated in the same manner as described in Example 1-(3) to give 1-cyclopropyl-6-fluoro-7-(3-methylamino-1-pyrrolidinyl)-1,4-dihydro-4-oxo-1,8-naphthyridine-3-carboxylic acid (800 mg), m.p. 233°–235° C. (decompn.).

(4) The ester (833 mg) obtained in (1) was treated in the same manner as described in Example 1-(4) to give 1-cyclopropyl-6-fluoro-7-(3-methylamino-1-pyrrolidinyl)-1,4-dihydro-4-oxo-1,8-naphthyridine-3-carboxylic acid (593 mg), m.p. 233°–235° C. (decompn.).

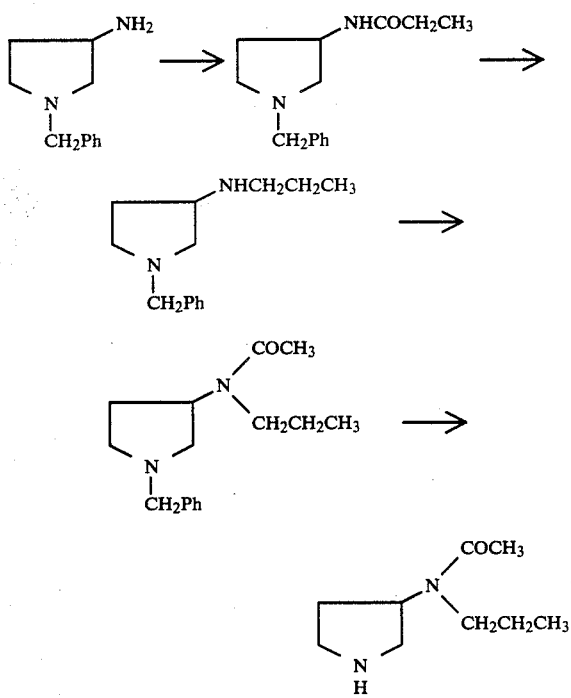

In the same manner as described in Reference Example 2 except that n-propionic anhydride is used in place of formic acid and formamide, 3-(N-acetyl-N-n-propylamino)pyrrolidine can be prepared.

EXAMPLE 3

Preparation of 1-cyclopropyl-6-fluoro-7-(3-n-propylamino-1-pyrrolidinyl)-1,4-dihydro-4-oxo-1,8-naphthyridine-3-carboxylic acid

EXAMPLE 4

Preparation of 7-(3-amino-4-methyl-1-pyrrolidinyl)-1-cyclopropyl-6-fluoro-1,4-dihydro-4-oxo-1,8-naphthyridine-3-carboxylic acid hydrochloride (by the substitution reaction A)

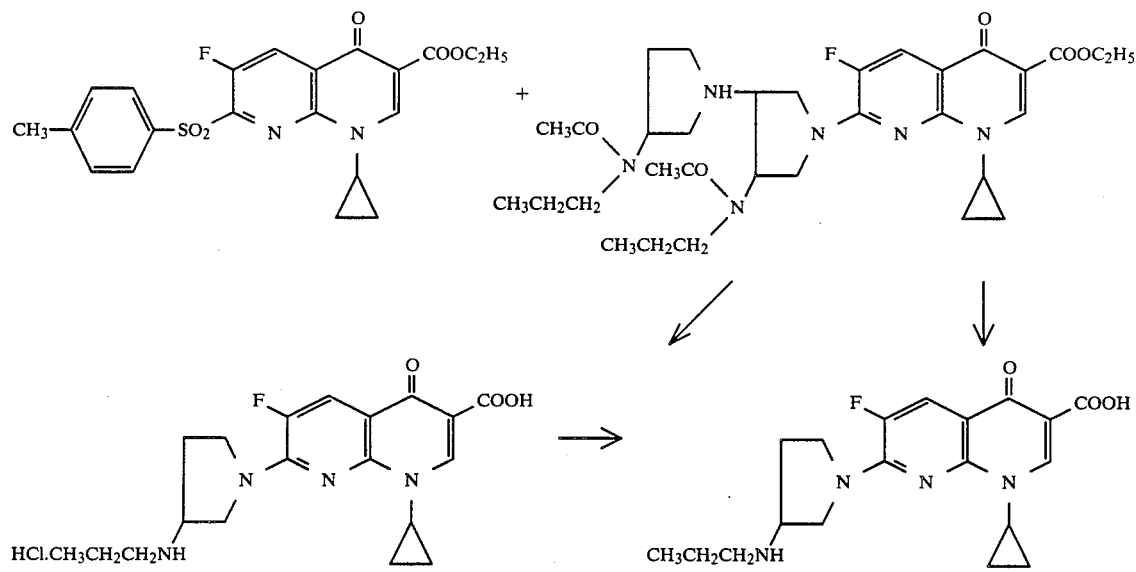

In the same manner as described in Example 2-(1), except that N-acetyl-N-n-propylaminopyrrolidine is used in place of N-acetyl-N-methylaminopyrrolidine, 1-cyclopropyl-6-fluoro-7-(3-n-propylamino-1-pyrrolidinyl)-1,4-dihydro-4-oxo-1,8-naphthyridine-3-carboxylic acid can be prepared.

REFERENCE EXAMPLE 4

Preparation of a starting compound of formula (III)

3-Acetylamino-4-methylpyrrolidine

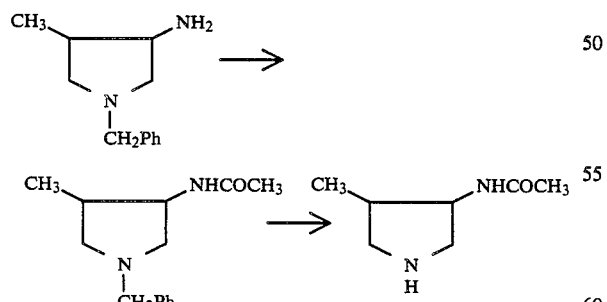

3-Amino-1-benzyl-4-methylpyrrolidine (Japanese Laid-Open Patent Publication No. 22699/1980) was allowed to react with acetic anhydride to give 3-acetylamino-1-benzyl-4-methylpyrrolidine; IR 3300, 1650 cm$^{-1}$. This compound was hydrogenated catalytically in the presence of 5% palladium-carbon to give 3-acetylamino-4-methylpyrrolidine as an oil.

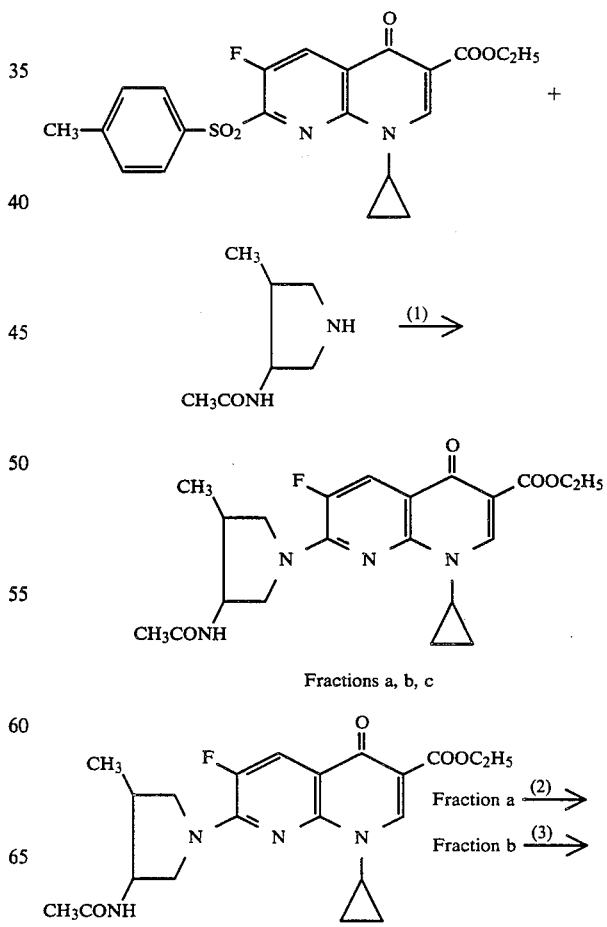

Fractions a, b, c

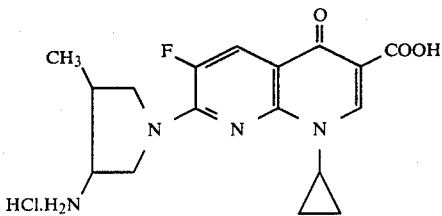

The numbers of the reaction steps described below correspond to the numbers in the above scheme.

(1) A mixture of ethyl 7-(p-tolylsulfonyl)-1-cyclopropyl-6-fluoro-1,4-dihydro-4-oxo-1,8-naphthyridine-3-carboxylate (4.3 g), 3-acetylamino-4-methylpyrrolidine (mixture of cis and trans forms) (1.85 g), sodium bicarbonate (1.26 g), and acetonitrile (60 ml) was refluxed for 1 hour. After evaporation of the solvent under reduced pressure, water was added to the residue and the mixture was extracted with chloroform. The extracts were washed with diluted hydrochloric acid and then with water, and dried over anhydrous sodium sulfate. After evaporation of the solvent, the residue was chromatographed on silica gel to give the following three fractions.

Fraction (a): stereoisomer A, 1.1 g.

Fraction (b): mixture of stereoisomers B and a small amount of stereoisomer A, 2.9 g.

Fraction (c): stereoisomer B, 0.1 g.

Fractions (a) and (c) were each recrystallized from ethanol-isopropyl ether to give the stereoisomer A, m.p. 280°–282.5° C., and the stereoisomer B, m.p. 209°–210° C., of ethyl 7-(3-acetylamino-4-methyl-1-pyrrolidinyl)-1-cyclopropyl-6-fluoro-1,4-dihydro-4-oxo-1,8-naphthyridine-3-carboxylate, respectively.

(2) A mixture of the ester, stereoisomer A (0.97 g), and 20% hydrochloric acid (10 ml) was refluxed for 3 hours. After evaporation under reduced pressure, ethanol was added to the residue, and the resulting crystals were filtered and recrystallized from water-ethanol to give a carboxylic acid hydrochloride, i.e. 7-(3-amino-4-methyl-1-pyrrolidinyl)-1-cyclopropyl-6-fluoro-1,4-dihydro-4oxo-1,8-naphthyridine-3-carboxylic acid hydrochloride (0.57 g), corresponding to the stereoisomer A, m.p. 234°–238° C. (decompn.). NMR (D₂O): δ1.32 (3H, d, J=7 Hz, CH₃), 7.42 (1H, d, J=13 Hz, C₅—H), 8.40 (1H, s, C₂—H).

(3) The fraction (b) obtained in (1) (2.9 g) was treated in the same manner as described in (2) to give 7-(3-amino-4-methyl-1-pyrrolidinyl)-1-cyclopropyl-6-fluoro-1,4-dihydro-4-oxo-1,8-naphthyridine-3carboxylic acid hydrochloride (2.02 g), m.p. 270°–278° C. (decompn.). NMR (D₂O): δ1.32 (3H, d, J=7 Hz, CH₃), 7.38 (1H, d, J=13 Hz, C₅—H), 8.41 (1H, s, C₂—H).

This compound was found to be a mixture of 6% and 94% of the carboxylic acid hydrochlorides corresponding to the stereoisomers A and B, respectively, from the result of HPLC analysis.

REFERENCE EXAMPLE 5

Preparation of a starting compound of formula (III)

3-Acetylamino-2-methylpyrrolidine

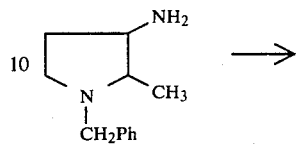

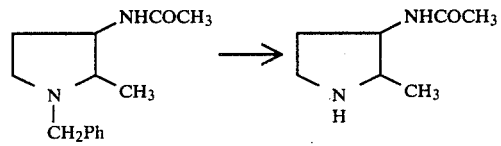

3-Amino-1-benzyl-2-methylpyrrolidine [Japanese Laid-Open Patent Publication No. 22699/1980] was allowed to react with acetic anhydride to give 3-acetylamino-1-benzyl-2-methylpyrrolidine, m.p. 51°–54° C. This compound was hydrogenated catalytically in the presence of 5% palladium-carbon to give 3-acetylamino-2-methylpyrrolidine as an oil.

EXAMPLE 5

Preparation of 7-(3-amino-2-methyl-1-pyrrolidinyl)-1-cyclopropyl-6-fluoro-1,4-dihydro-4-oxo-1,8-naphthyridine-3-carboxylic acid hydrochloride (by the substitution reaction A)

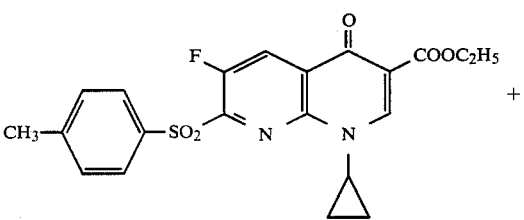

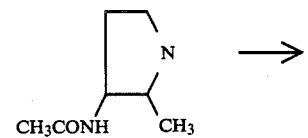

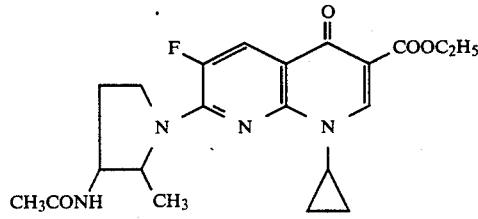

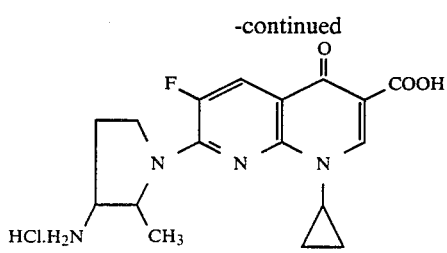

In the same manner as described in Example 4-(1), except that 3-acetylamino-2-methylpyrrolidine was used in place of 2-acetylamino-4-methylpyrrolidine, 7-(3-amino-2-methyl-1-pyrrolidinyl)-1-cyclopropyl-6-fluoro-1,4-dihydro-4-oxo-1,8-naphthyridine-3-carboxylic acid hydrochloride was prepared. Stereoisomer A (3/2 hydrate), m.p. 215°–217° C., NMR (NaOD—D$_2$O): δ1.03 (3H, d, J=6 Hz, CH$_3$), 7.63 (1H, d, J=13 Hz, C$_5$—H), 8.32 (1H, s, C$_2$—H) and a mixture of the stereoisomers A and B (3/2 hydrate), m.p. 276°–280° C. (decompn.) (A:B=1:4 by HPLC analysis). NMR of the stereoisomer B (NaOD—D$_2$O): δ1.17 (3H, d, J=6 Hz, CH$_3$), 7.75 (1H, d, J=13 Hz, C$_5$—H), 8.33 (1H, s, C$_2$—H).

REFERENCE EXAMPLE 6

Prepartion of a starting compound of formula (III)

4-Acetylamino-2-methylpyrrolidine

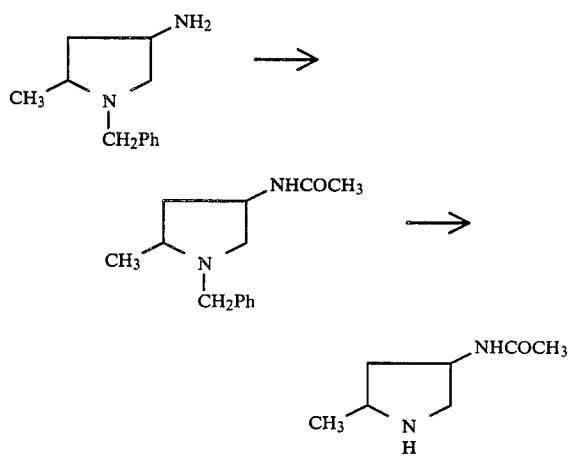

In the same manner as described in Reference Example 4, except that 4-amino-1-benzyl-2-methylpyrrolidine was used in place of 3-amino-1-benzyl-4-methylpyrrolidine, 4-acetylamino-2-methylpyrrolidine was prepared.

EXAMPLE 6

Preparation of 7-(4-amino-2-methyl-1-pyrrolidinyl)-1-cyclopropyl-6-fluoro-1,4-dihydro-4-oxo-1,8-naphthyridine-3-carboxylic acid hydrochloride (by the substitution reaction A)

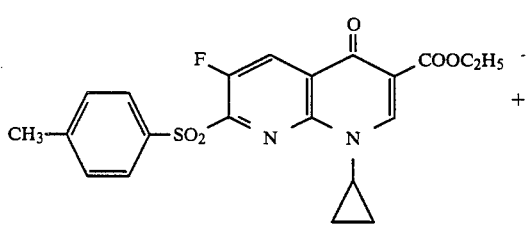
+
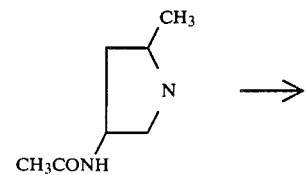
↓
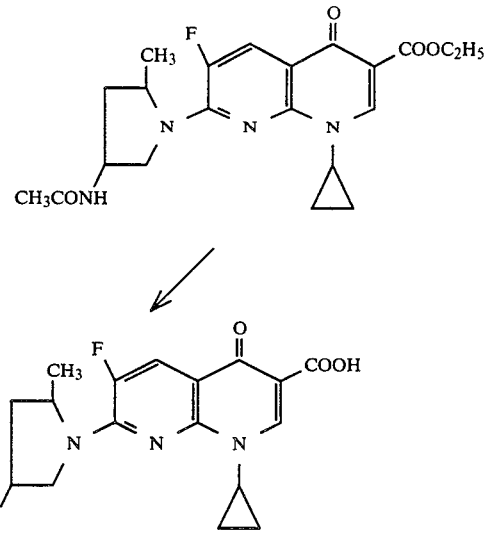

In the same manner as described in Example 4-(1), except that 4-acetylamino-2-methylpyrrolidine was used in place of 3-acetylamino-4-methylpyrrolidine, 7-(4-amino-2-methyl-1-pyrrolidinyl)-1-cyclopropyl-6-fluoro-1,4-dihydro-4-oxo-1,8-naphthyridine-3-carboxylic acid hydrochloride was prepared. Stereoisomer A (5/4 hydrate), m.p. 263°–267° C. (decompn.), NMR (NaOD—D$_2$O): δ1.29 (3H, d, J=6 Hz, CH$_3$), 7.74 (1H, d, J=13 Hz, C$_5$—H), 8.39 (1H, s, C$_2$—H) and a mixture of the stereoisomers A and B (2 hydrate), m.p.—205°–208° C. and 241°–244° C. (decompn.) (A:B=3:2 by HPLC analysis). NMR of the stereoisomer B (NaOD—D$_2$O): δ1.28 (3H, d, J=6 Hz, CH$_3$), 7.70 (1H, d, J=13 Hz, C$_5$—H), 8.39 (1H, s, C$_2$—H).

REFERENCE EXAMPLE 7

Preparation of a starting compound of formula (III)

3-Acetylamino-3-methylpyrrolidine

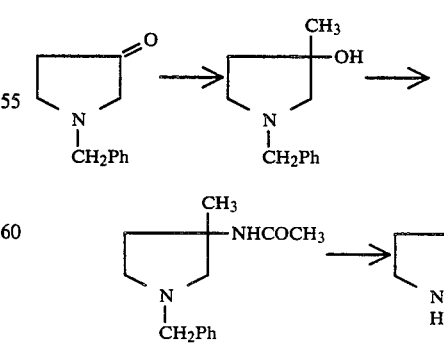

1-Benzyl-3-pyrrolidone [J. Org. Chem., 30., 740 (1965)] was allowed to react with methylmagnesium iodide to give 1-benzyl-3-hydroxy-3-methylpyrrolidine as an oil, b.p. 106° C./0.5 mmHg. This compound was treated with a mixture of acetonitrile and concentrated sulfuric acid under ice cooling to give 3-acetylamino-1-benzyl-3-methylpyrrolidine, m.p. 105°–106° C. This compound was hydrogenated catalytically in the presence of 5% palladium-carbon to give 3-acetylamino-3-methylpyrrolidine as an oil.

EXAMPLE 7

Preparation of 7-(3-amino-3-methyl-1-pyrrolidinyl)-1-cyclopropyl-6-fluoro-1,4-dihydro-4-oxo-1,8-naphthyridine-3-carboxylic acid hydrochloride (by the substitution reaction A)

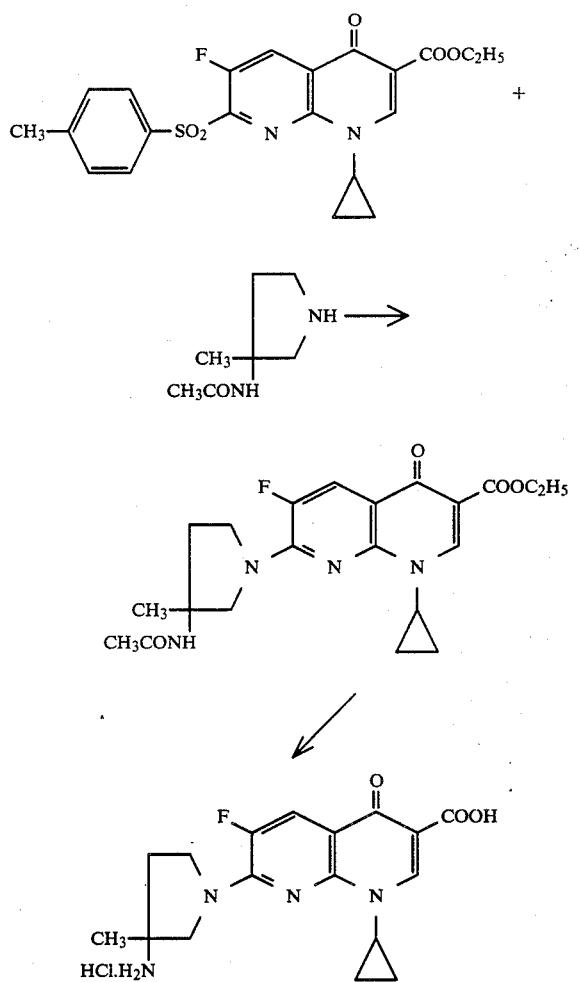

In the same manner as described in Example 4-(1), except that 3-acetylamino-3-methylpyrrolidine was used in place of 3-acetylamino-4-methylpyrrolidine, 7-(3-amino-3-methyl-1-pyrrolidinyl)-1-cyclopropyl-6-fluoro-1,4-dihydro-4-oxo-1,8-naphthyridine-3-carboxylic acid hydrochloride (5/4 hydrate) was prepared, m.p. 285°–287° C. (decompn.). NMR (D$_2$O): δ1.74 (3H, s, CH$_3$), 7.45 (1H, d, J=13 Hz, C$_5$—H), 8.42 (1H, s, C$_2$—H).

REFERENCE EXAMPLE 8

Preparation of a starting compound of formula (III) 3-(N-Acetyl-N-methylamino)-4-methylpyrrolidine

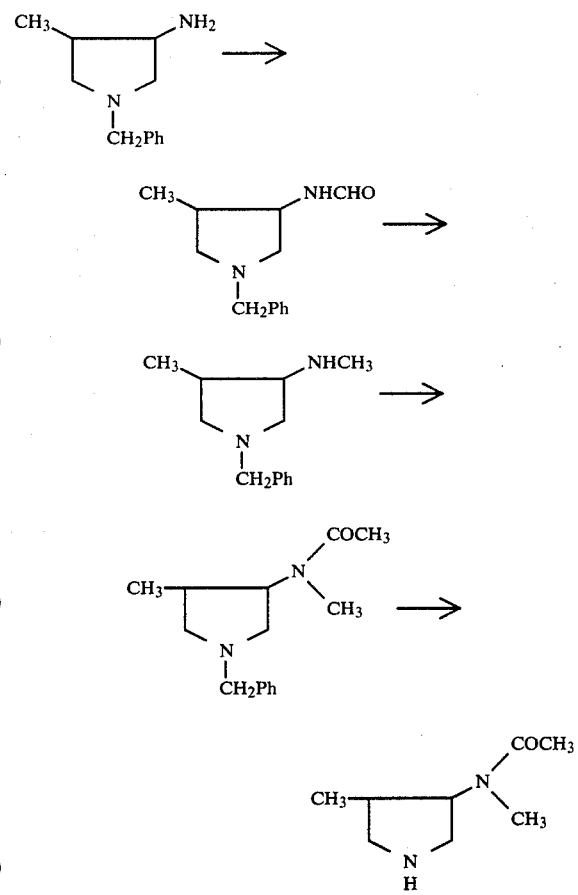

In the same manner as described in Reference Example 2, except that 3-amino-1-benzyl-4-methylpyrrolidine [see Japanese Laid-Open Patent Publication No. 22699/1980] was used in place of 3-amino-1-benzylpyrrolidine, 3-(N-acetyl-N-methylamino)-4-methylpyrrolidine was prepared.

EXAMPLE 8

Preparation of 1-cyclopropyl-6-fluoro-7-(4-methyl-3-methylamino-1-pyrrolidinyl)-1,4-dihydro-4-oxo-1,8-naphthyridine-3-carboxylic acid hydrochloride (by the substitution reaction A)

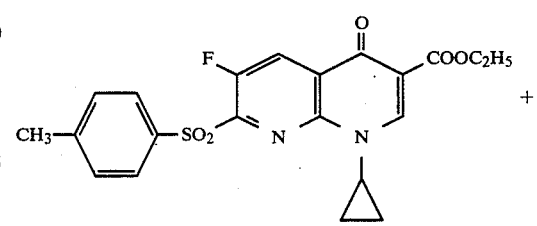

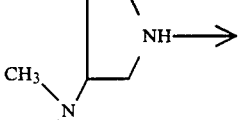

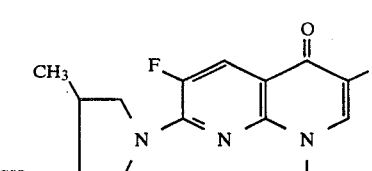

In the same manner as described in Example 4-(1), except that 3-(N-acetyl-N-methlamino)-4-methylpyrrolidine was used in place of 3-acetylamino-4-methylpyrrolidine, 1-cyclopropyl-6-fluoro-7-(4-methyl-3-methylamino-1-pyrrolidinyl)-1,4-dihydro-4-oxo-1,8-naphthyridine-3-carboxylic acid hydrochloride (5/4 hydrate) was prepared, m.p. 258°–277° C. (decompn.). NMR (NaOD—D$_2$O): δ1.07 (3H, d, J=6 Hz, CH$_3$), 2.34 (3H, s, N—CH$_3$), 7.52 (1H, d, J=13 Hz, C$_5$—H), 8.27 (1H, s, C$_2$—H).

REFERENCE EXAMPLE 9

Preparation of a starting compound of formula (II)

3-Acetylamino-4-ethylpyrrolidine

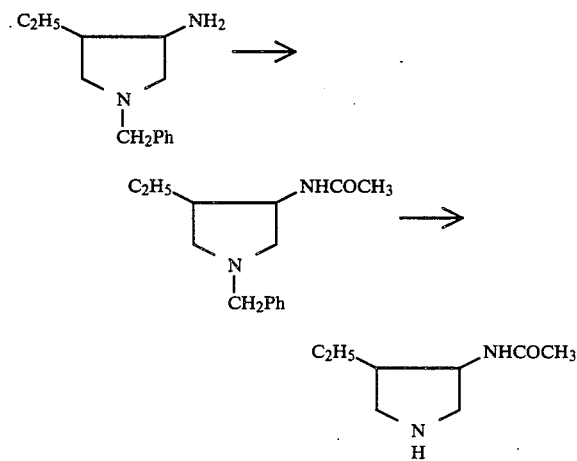

In the same manner as described in Reference Example 4, except that 3-amino-1-benzyl-4-ethylpyrrolidine was used in place of 3-amino-1-benzyl-4-methylpyrrolidine, 3-acetylamino-4-ethylpyrrolidine was prepared.

EXAMPLE 9

Preparation of 7-(3-amino-4-ethyl-1-pyrrolidinyl)-1-cyclopropyl-6-fluoro-1,4-dihydro-4-oxo-1,8-naphthyridine-3-carboxylic acid hydrochloride (by the substitution reaction A)

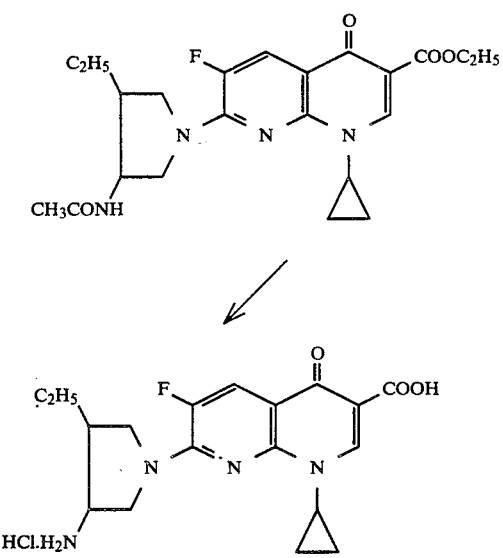

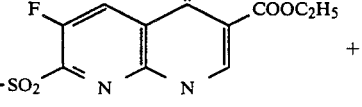

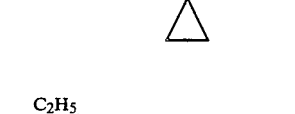

In the same manner as described in Example 4-(1), except that 3-acetylamino-4-ethylpyrrolidine was used in place of 3-acetylamino-4-methylpyrrolidine, 7-(3-amino-4-ethyl-1-pyrrolidinyl)-1-cyclopropyl-6-fluoro-1,4-dihydro-4-oxo-1,8-naphthyridine-3-carboxylic acid hydrochloride was prepared, m.p. 232°–237° C. (decompn.). NMR (NaOD—D$_2$O): δ0.95 (3H, t, J=7 Hz, —CH$_2$CH$_3$), 1.66 (2H, q, J=7 Hz, —CH$_2$CH$_3$), 7.55 (1H, d, J=13 Hz, C$_5$—H), 8.33 (1H, s, C$_2$—H).

REFERENCE EXAMPLE 10

Preparation of a starting compound of formula (II)

Ethyl 7-chloro-1-cyclopropyl-6-fluoro-1,4-dihydro-4-oxo-1,8-naphthyridine-3-carboxylate

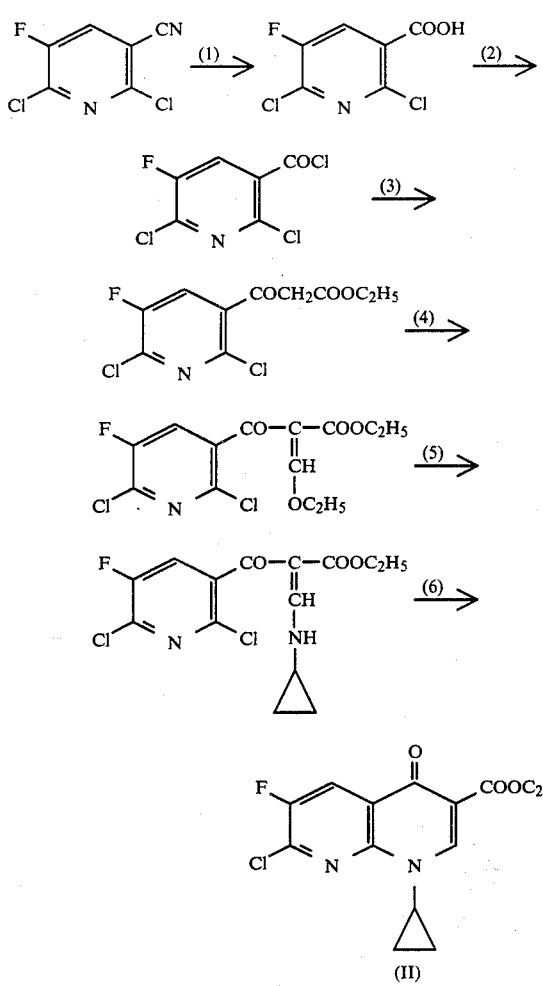

The numbers of the reaction steps described below correspond to the numbers in the above scheme.

(1) A known compound 2,6-dichoro-5-fluoronicotinonitrile (60 g) in concentrated sulfuric acid was heated at 65°–75° C. for 1 hour. Water was added to the reaction mixture, which was then heated at 100°–110° C. for 2 hours to give 2,6-dichloro-5-fluoronicotinic acid (59.8 g), m.p. 155°–156° C.

(2) The above compound was treated with thionyl chloride to give 2,6-dichloro-5-fluoronicotinoyl chloride (47.5 g) as an oil.

(3) In dry ether, the above compound was allowed to react with diethyl ethoxymagnesiummalonate to give diethyl 2,6-dichloro-5-fluoronicotinoylmalonate as an oil. To this were added water and a catalytic amount of p-toluenesulfonic acid, and then the mixture was heated at 140° C. for 2 hours to give ethyl 3-(2,6-dichloro-5-fluoropyridin-3-yl)-3-oxopropionate (46 g), m.p. 69°–70° C.

(4) The above compound (40 g) was treated with ethyl orthoformate and acetic anhydride to give ethyl 2-(2,6-dichloro-5-fluoronicotinoyl)-3-ethoxyacrylate (42 g) as an oil.

(5) The above compound in ethanol was allowed to react with cyclopropylamine to give ethyl 2-(2,6-dichloro-5-fluoronicotinoyl)-3-cyclopropylaminoacrylate (42.4 g), m.p. 129°–130° C.

(6) In dry dioxane, the above compound (21 g) was allowed to react with potassium tert.-butoxide to give ethyl 7-chloro-1-cyclopropyl-6-fluoro-1,4-dihydro-4-oxo-1,8-naphthyridine-3-carboxylate (17.5 g), m.p. 176°–178° C.

The starting materials (II) which have any substituents (—COOY′) at the 3-position of their naphthyridine ring other than —COOC$_2$H$_5$ can also be prepared in the same manner as described above.

REFERENCE EXAMPLE 11

Preparation of a starting compound of formula (II)

Ethyl 7-chloro-1-cyclopropyl-6-fluoro-1,4-dihydro-4-oxo-1,8-naphthyridine-3-carboxylate

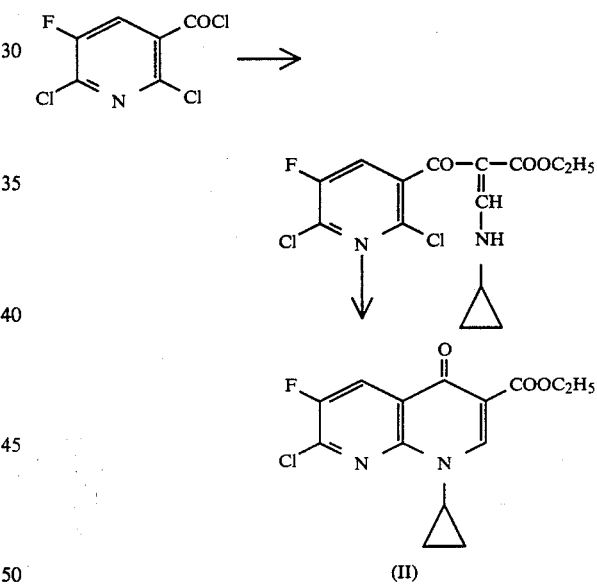

In dry dioxane, 2,6-dichloro-5-fluoronicotinoyl chloride, prepared in Reference Example 10-(2), was allowed to react with ethyl β-cyclopropylaminoacrylate in the presence of triethylamine to give ethyl 2-(2,6-dichloro-5-fluoronicotinoyl)-3-cyclopropylaminoacrylate, m.p. 129°–130° C.

This compound was treated in dry dioxane with potassium tert.-butoxide to give ethyl 7-chloro-1-cyclopropyl-6-fluoro-1,4-dihydro-4-oxo-1,8-naphthyridine-3-carboxylate, m.p. 176°–178° C.

The starting materials (II) which have any substituents (—COOY′) at the 3-position of their naphthyridine ring other than —COOC$_2$H$_5$ can also be prepared in the same manner as described above.

EXAMPLE 10

Preparation of 7-(3-amino-1-pyrrolidinyl)-1-cyclopropyl-6-fluoro-1,4-dihydro-4-oxo-1,8-naphthyridine-3-carboxylic acid hydrochloride (by the ssubstitution reaction A)

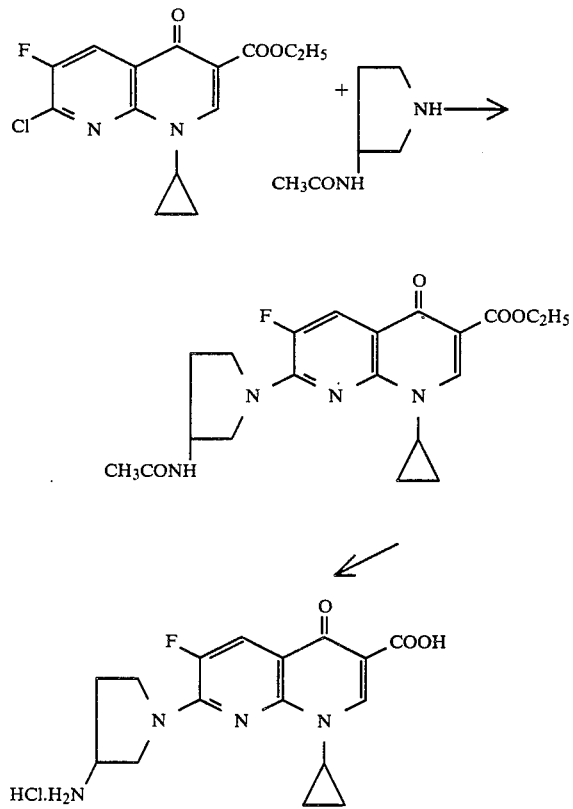

A mixture of ethyl 7-chloro-1-cyclopropyl-6-fluoro-1,4-dihydro-4-oxo-1,8-naphthyridine-3-carboxylate (1.24 g), 3-acetylaminopyrrolidine (563 mg), sodium bicarbonate (437 mg) and acetonitrile (40 ml) was refluxed for 30 minutes. After evaporation to dryness under reduced pressure, water was added to the residue. The resulting crystals were filtered and recrystallized from ethanolisopropyl ether to give ethyl 7-(3-acetylamino-1-pyrrolidinyl)-1-cyclopropyl-6-fluoro-1,4-dihydro-4-oxo-1,8-naphthyridine-3-carboxylate (1.50 g), m.p. 246°–248° C.

This compound was hydrolyzed in the same manner as described in Example 1-(2) to give 7-(3-amino-1-pyrrolidinyl)-1-cyclopropyl-6-fluoro-1,4-dihydro-4-oxo-1,8-naphthyridine-3-carboxylic acid hydrochloride (1.15 mg), m.p. 275°–280° C. (decompn.).

REFERENCE EXAMPLE 12

Preparation of a starting compound of formula (IV) for use in reaction B

Ethyl 6-(3-acetylamino-1-pyrrolidinyl)-2-[N-cyclopropyl-N-(2-ethoxycarbonylethyl)amino]-5-fluoronicotinate

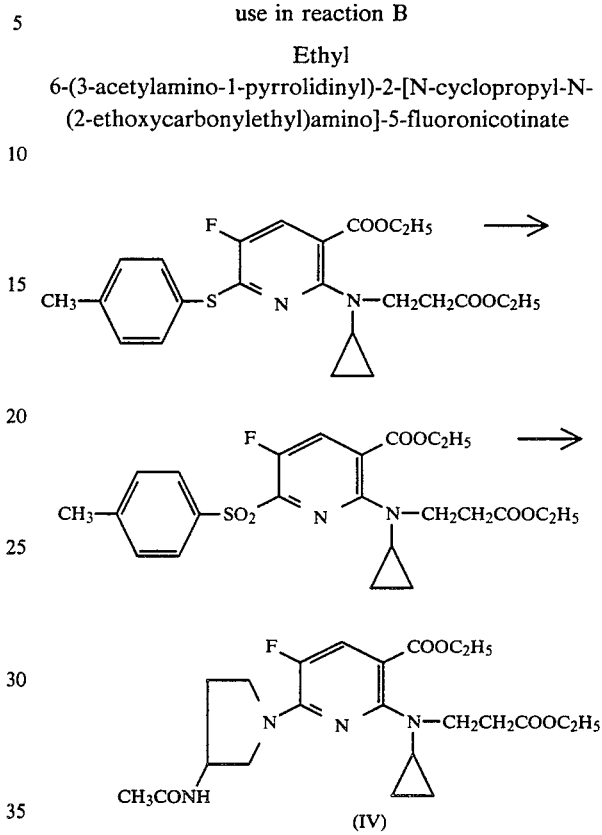

Ethyl 6-(p-tolylthio)-2-[N-cyclopropyl-N-(2-ethoxycarbonylethyl)amino]-5-fluoronicotinate (16.0 g) prepared in Reference Example 1-(4), was oxidized with m-chloroperbenzoid acid to give ethyl 6-(p-tolylsulfonyl)-2-[N-cyclopropyl-N-(2-ethoxycarbonylethyl)amino]-5-fluoronicotinate (17.0 g). This compound (9.56 g) was heated at 120° C. for 2 hours in dimethylformamide with 3-acetylaminopyrrolidine (3.84 g) in the presence of sodium bicarbonate (2.52 g) to give ethyl 6-(3-acetylamino-1-pyrrolidinyl)-2-[N-cyclopropyl-N-(2-ethoxycarbonylethyl)-amino]-5-fluoronicotinate (8.0 g) as an oil.

EXAMPLE 11

Preparation of 7-(3-amino-1-pyrrolidinyl)-1-cyclopropyl-6-fluoro-1,4-dihydro-4-oxo-1,8-naphthyridine-3-carboxylic acid hydrochloride (by the Dieckmann reaction B)

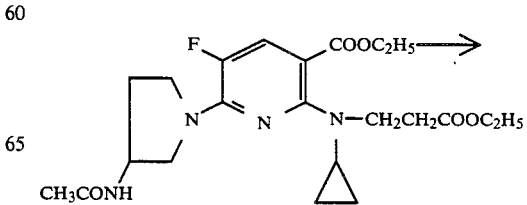

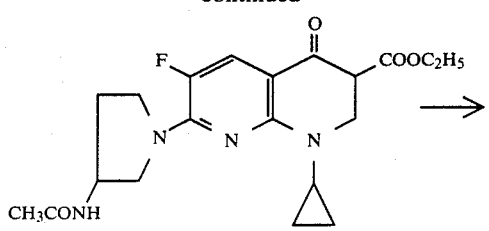

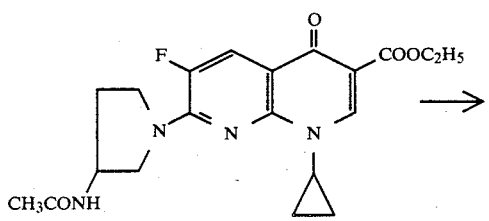

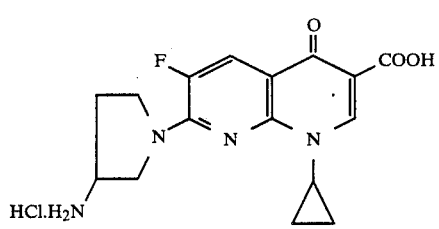

Ethyl 6-(3-acetylamino-1-pyrrolidinyl)-2-[N-cyclopropyl-N-(2-ethoxycarbonylethyl)amino]-5-fluoronicotinate (5.0 g) was dissolved in dry tert.-butyl alcohol (60 ml). To this solution was added potassium tert.-butoxide (3.1 g), and the mixture was stirred at room temperature for 1.5 hours. After evaporation of the solvent under reduced pressure, aqueous acetic acid was added to neutralize the residue, followed by its extraction with chloroform (70 ml). The extract was then dried over anhydrous sodium sulfate. It was found that the reaction product contained in this solution was ethyl 7-(3-acetylamino-1-pyrrolidinyl)-1-cyclopropyl-6-fluoro-1,2,3,4-tetrahydro-4-oxo-1,8-naphthyridine-3-carboxylate by its NMR spectrum.

To this chloroform solution was added bromine (1.8 g) dropwise at room temperature with stirring. After stirring for 1 hour, the reaction mixture was washed sequentially with aqueous sodium thiosulfate, aqueous sodium bicarbonate, and water, followed by drying over anhydrous sodium sulfate. The chloroform was evaporated, ethyl acetate was added to the residue, and the resulting crystals were cooled and filtered to give ethyl 7-(3-acetylamino-1-pyrrolidinyl)-1-cyclopropyl-6-fluoro-1,4-dihydro-4-oxo-1,8-naphthyridine-3-carboxylate (3.2 g), m.p. 246°–248° C.

This compound was hydrolyzed in the same manner as described in Example 1-(2) to give 7-(3-amino-1-pyrrolidinyl)-1-cyclopropyl-6-fluoro-1,4-dihydro-4-oxo-1,8-naphthyridine-3-carboxylic acid hydrochloride (2.4 g), m.p. 275°–280° C. (decompn.).

REFERENCE EXAMPLE 13

Preparation of a starting compound of formula (VI) for use in reaction C

Ethyl 2-[6-(3-acetylamino-1-pyrrolidinyl)-2-chloro-5-fluoronicotinoyl]-3-cyclopropylaminoacrylate

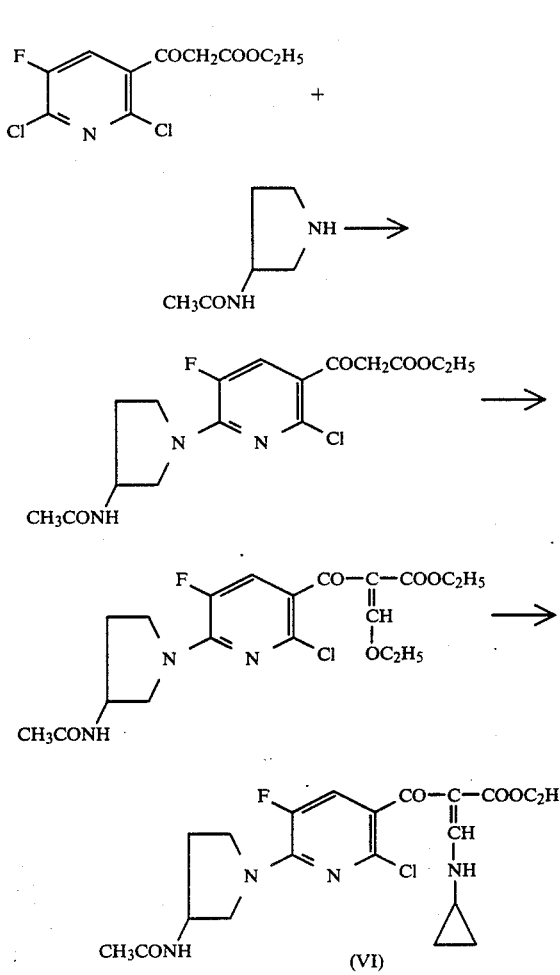

Ethyl 3-(2,6-dichloro-5-fluoropyridin-3-yl)-3-oxopropionate (1.4 g) prepared in Reference Example 10-(3) was allowed to react with 3-acetylaminopyrrolidine to give ethyl 3-[6-(3-acetylamino-1-pyrrolidinyl)-2-chloro-5-fluoropyridin-3-yl]-3-oxopropionate (0.78 g) as a oil. This compound (0.74 g) was treated with ethyl orthoformate and acetic anhydride, and the resulting oil, ethyl 2-[6-(3-acetylamino-1-pyrrolidinyl)-2-chloro-5-fluoronicotinoyl]-3-ethoxyacrylate, was allowed to react with cyclopropylamine to give ethyl 2-[6-(3-acetylamino-1-pyrrolidinyl)-2-chloro-5-fluoronicotinoyl]-3-cyclopropylaminoacrylate (0.43 g) as an amorphous powder, m.p. 71°–75° C.

EXAMPLE 12

Preparation of 7-(3-amino-1-pyrrolidinyl)-1-cyclopropyl-6-fluoro-1,4-dihydro-4-oxo-1,8-naphthyridine-3-carboxylic hydrochloride (by the cyclization reaction C)

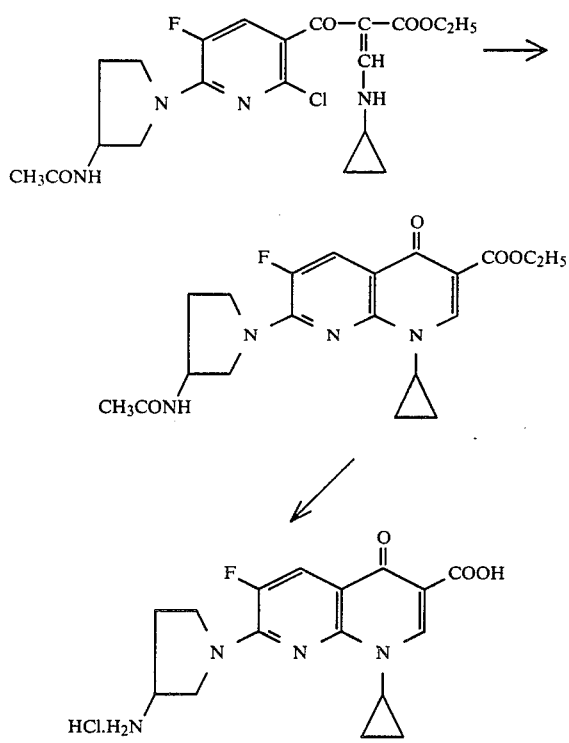

Ethyl 2-[6-(3-acetylamino-1-pyrrolidinyl)-2-chloro-6-fluoronicotinoyl]-3-cyclopropylaminoacrylate (0.4 g) was treated in dioxane with 60% sodium hydride to give ethyl 7-(3-acetylamino-1-pyrrolidinyl)-1-cyclopropyl-6-fluoro-1,4-dihydro-4-oxo-1,8-naphthyridine-3-carboxylate (0.25 g), m.p. 246°–248° C.

This compound was hydrolyzed in the same manner as described in Example 1-(2) to give 7-(3-amino-1-pyrrolidinyl)-1-cyclopropyl-6-fluoro-1,4-dihydro-4-oxo-1,8-naphthyridine-3-carboxylic acid hydrochloride (0.19 g), m.p. 275°–280° C. (decompn.).

EXAMPLE 13

Preparation of ethyl 7-(3-amino-4-methtyl-1-pyrrolidinyl)-1-cyclopropyl-6-fluoro-1,4-dihydro-4-oxo-1,8-naphthyridine-3-carboxylate

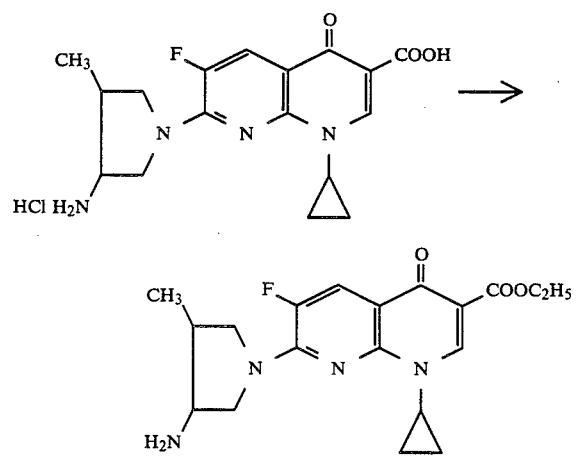

7-(3-Amino-4-methyl-1-pyrrolidinyl)-1-cyclopropyl-6-fluoro-1,4-dihydro-4-oxo-1,8-naphthyridine-3-car-boxylic acid hydrochloride (6.6 g) was suspended in absolute ethanol. Sulfuric acid (7 g) was added to the suspension and the mixture was refluxed for 1 hour with stirring. After evaporation of ethanol (ca. 20 ml), absolute ethanol (20 ml) was added and the mixture was again refluxed. This operation was repeated three times and then the mixture was refluxed for 15 hours with stirring. After evaporation of ethanol, chloroform and 20% aqueous sodium hydroxide solution was added to the residue, and the mixture was adjusted to pH > 9. The organic layer was separated, chloroform was evaporated under reduced pressure, and the residue was recrystallized from ethyl acetate to give ethyl 7-(3-amino-4-methyl-1-pyrrolidinyl)-1-cyclopropyl-6-fluoro-1,4-dihydro-4-oxo-1,8naphthyridine-3-carboxylate (4.3 g), m.p. 148°–150.5° C.

EXAMPLE 14

Preparation of ethyl 7-(3-amino-1-pyrrolidinyl)-1-cyclopropyl-6-fluoro-1,4-dihydro-4-oxo-1,8-naphthyridine-3-carboxylate

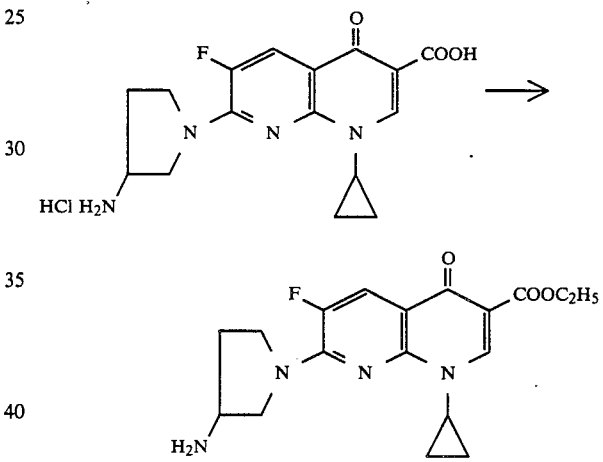

In the same manner as described in Example 13, except that 7-(3-amino-1-pyrrolidinyl)-1-cyclopropyl-6-fluoro-1,4-dihydro-4-oxo-1,8-naphthyridine-3-carboxylic acid hydrochloride was used in place of 7-(3-amino-4-methyl-1-pyrrolidinyl)-1-cyclopropyl-6-fluoro-1,4-dihydro-4-oxo-1,8-naphthyridine-3-carboxylic acid hydrochloride, ethyl 7-(3-amino-1-pyrrolidinyl)-1-cyclopropyl-6-fluoro-1,4-dihydro-4-oxo-1,8-naphthyridine-3-carboxylate was prepared, m.p. 144°–146° C.

EXAMPLE 15

Preparation of n-propyl 7-(3-amino-1-pyrrolidinyl)-1-cyclopropyl-6-fluoro-1,4-dihydro-4-oxo-1,8-naphthyridine-3-carboxylate

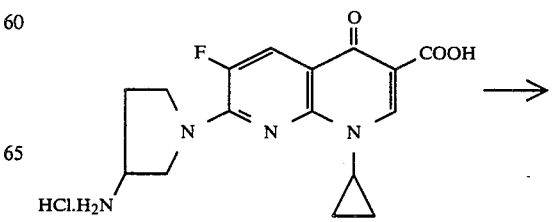

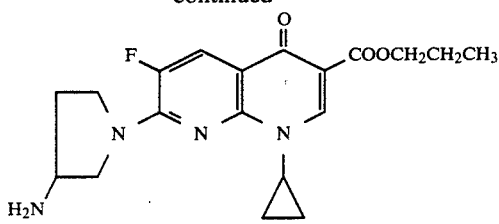

In the same manner as described in Example 13, except that 7-(3-amino-1-pyrrolidinyl)-1-cyclopropyl-6-fluoro-1,4-dihydro-4-oxo-1,8-naphthyridine-3-carboxylic acid hydrochloride and n-propyl alcohol were used in place of 7-(3-amino-4-methyl-1-pyrrolidinyl)-1-cyclopropyl-6-fluoro-1,4-dihydro-4-oxo-1,8-naphthyridine-3-carboxylic acid hydrochloride and absolute ethanol, n-propyl 7-(3-amino-1-pyrrolidinyl)-1-cyclopropyl-6-fluoro-1,4-dihydro-4-oxo-1,8-naphthyridine-3-carboxylate was prepared, m.p. 125°-126° C.

EXAMPLE 16

Preparation of ethyl 1-cyclopropyl-6-fluoro-7-(3-methylamino-1-pyrrolidinyl)-1,4-dihydro-4-oxo-1,8-naphthyridine-3-carboxylate

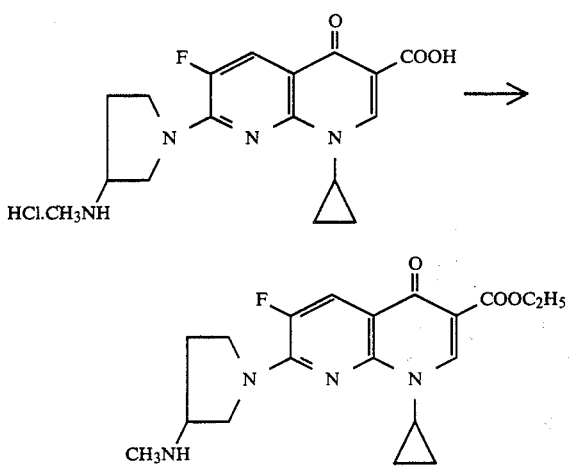

In the same manner as described in Example 13, except that 1-cyclopropyl-6-fluoro-7-(3-methylamino-1-pyrrolidinyl)-1,4-dihydro-4-oxo-1,8-naphthyridine-3-carboxylic acid hydrochloride was used in place of 7-(3-amino-4-methyl-1-pyrrolidinyl)-1-cyclopropyl-6-fluoro-1,4-dihydro-4-oxo-1,8-naphthyridine-3-carboxylic acid hydrochloride, ethyl 1-cyclopropyl-6-fluoro-7-(3-methylamino-1-pyrrolidinyl)-1,4-dihydro-4-oxo-1,8-naphthyridine-3-carboxylate was prepared, m.p. 164°-165.5° C.

Examples 17 to 19 show the pharmaceutical preparations containing the compounds of this invention as active ingredients. Compounds 1a and 3a are as defined hereinafter.

EXAMPLE 17

| Compound 1a or 3a | 250 g |
| Starch | 50 g |
| Lactose | 35 g |
| Talc | 15 g |

The above components were blended with ethanol and granulated and filled into 1,000 capsules in accordance with conventional methods.

EXAMPLE 18

| Compound 1a or 3a | 250 g |
| Starch | 54 g |
| Calcium carboxymethyl cellulose | 40 g |
| Microcrystalline cellulose | 50 g |
| Magnesium stearate | 6 g |

The above comonents were blended with ethanol, granulated and made into tablets in a manner known per se. Thus, 1,000 tablets each weighing 400 mg were formed.

EXAMPLE 19

| Compound 1a | 50 g |
| Lactic acid | 120 g |

The above components were dissolved in distilled water sufficient to make ten liters solution. The solution was adjusted to pH about 4 with an aqueus sodium hydroxide solution, and then filled in ampules (10 ml) to make an injectable solution.

The chemotherapeutic activities of the compounds of this invention are shown in Examples 20 and 21 hereinbelow in comparison with known antibacterial agents. The compounds tested comprise:

Compound 1a: 7-(3-amino-1-pyrrolidinyl)-1-cyclopropyl-6-fluoro-1,4-dihydro-4-oxo-1,8-naphthyridine-3-carboxylic acid hydrochloride, Compound 2a: 1-cyclopropyl-6-fluoro-7-(3-methylamino-1-pyrrolidinyl)-1,4-dihydro-4-oxo-1,8-naphthyridine-3-carboxylic acid hydrochloride, Compound 3a: 7-(3-amino-4-methyl-1-pyrrolidinyl)-1-cyclopropyl-6-fluoro-1,4-dihydro-4-oxo-1,8-naphthyridine-3-carboxylic acid hydrochloride which was obtained in Example 4-(3), Compound 4a: 7-(3-amino-3-methyl-1-pyrrolidinyl)-1-cyclopropyl-6-fluoro-1,4-dihydro-4-oxo-1,8-naphthyridine-3-carboxylic acid hydrochloride, Compound A: 7-(3-amino-1-pyrroldinyl)-1-ethyl-6-fluoro-1,4-dihydro-4-oxo-1,8-naphthyridine-3-carboxylic acid hydrochloride which is disclosed in Example 7 of U.S. Pat. 4,341,784, and Compound B: 1-ethyl-6-fluoro-7-(3-methylamino-1-pyrrolidinyl)-1,4-dihydro-4-oxo-1,8-naphthyridine-3-carboxylic acid hydrochloride which is disclosed in Example 6 of U.S. Pat. No. 4,341,784.

EXAMPLE 20

The antibacterial activity in vitro is shown in Table 1. The numerals in the table show minimum inhibitory concentrations (MIC) (μg/ml), calculated for free base. The minimum inhibitory concentrations were determined according to the agar dilution method recommeded by Japan Society of Chemotherapy (Chemotherapy, 29, 1, 76 (1981)).

TABLE 1

| Strains | In vitro antibacterial activity Compounds | | | | | |
|---|---|---|---|---|---|---|
| | 1a | 2a | 3a | 4a | A | B |
| S. aureus 209P JC-1 | 0.05 | 0.2 | 0.05 | 0.05 | 0.2 | 0.78 |
| S. aureus Terajima | 0.05 | 0.1 | 0.05 | 0.05 | 0.2 | 0.78 |
| S. pyogenes A65 | 0.2 | 0.39 | 0.2 | 0.2 | 1.56 | 12.5 |
| S. pyogenes Cook | 0.2 | 0.39 | 0.2 | 0.2 | 1.56 | 12.5 |
| E. coli NIHJ JC-2 | 0.0063 | 0.0125 | 0.0063 | 0.0125 | 0.1 | 0.2 |
| E. coli P-5101 | 0.0031 | 0.0125 | 0.0063 | 0.0125 | 0.05 | 0.2 |
| S. typhi 901 | 0.0063 | 0.025 | 0.0063 | 0.025 | 0.1 | 0.39 |
| S. paratyphi 1015 | 0.0063 | 0.0125 | 0.0125 | 0.0125 | 0.05 | 0.2 |
| S. schottmuelleri 8006 | 0.0031 | 0.0125 | 0.0063 | 0.0063 | 0.05 | 0.1 |
| S. sonnei EW 33 | 0.0031 | 0.0125 | 0.0063 | 0.0125 | 0.05 | 0.1 |
| P. morganii IFO 3848 | 0.0063 | 0.0125 | 0.0125 | 0.0125 | 0.1 | 0.2 |
| P. vulgaris OX-19 | 0.0125 | 0.05 | 0.025 | 0.025 | 0.1 | 0.2 |
| P. mirabilis IFO 3849-4 | 0.2 | 0.78 | 0.39 | 0.39 | 0.39 | 1.56 |
| P. rettgeri IFO 3850 | 0.025 | 0.1 | 0.025 | 0.05 | 0.2 | 0.78 |
| K. pneumoniae PCI 602 | 0.0031 | 0.0063 | 0.0031 | 0.0063 | 0.05 | 0.78 |
| E. aerogenes ATCC 13048 | 0.0125 | 0.05 | 0.025 | 0.05 | 0.2 | 0.39 |
| E. cloacae 963 | 0.0125 | 0.05 | 0.025 | 0.05 | 0.2 | 0.39 |
| S. marcescens IFO 3736 | 0.05 | 0.2 | 0.1 | 0.2 | 0.2 | 0.78 |
| P. aeruginosa IFO 3445 | 0.1 | 0.39 | 0.2 | 0.39 | 0.39 | 3.13 |
| P. aeruginosa NCTC 10490 | 0.1 | 0.39 | 0.2 | 0.2 | 0.39 | 3.13 |
| P. aeruginosa 12 | 0.1 | 0.2 | 0.2 | 0.2 | 0.39 | 3.13 |

EXAMPLE 21

In vivo efficacy against systemic infections in mice is shown in Table 2.

Compounds were each dissolved in deionized water. Each of the solutions was orally (po) or intravenously (iv) administered to mice infected with each of the test organisms under the conditions shown hereinbelow, and the median effective dose ($ED_{50}$) was calculated by probit analysis. The numerals in the table show $ED_{50}$ (mg/kg) value, calculated for free base.

Experimental conditions:

Mice: Male mice (ddY-S) weighing about 20 g Infection:
Streptococcus pneumoniae 1
 Intraperitoneal infection with $3 \times 10^3$ cells per mouse suspended in brain heart infusion broth.
Streptococcus pyogenes A65
 Intraperitoneal infection with $3 \times 10^7$ cells per mouse suspended in brain heart infusion broth.
Escherichia coli P-5101
 Intraperitoneal infection with about $9 \times 10^6$ cells per mouse suspended in trypto-soy broth with 4% mucin
Pseudomonas aeruginosa 12
 Intraperitoneal infection with about $5 \times 10^3$ cells per mouse suspended in trypto-soy broth with 4% mucin Medication:

Four times, immediately, 6, 24 and 30 hours after infection in case of Streptococcus pneumoniae 1 Twice, immediately and 6 hours after infection in case of other organisms Observation:

For 14 days in case of Streptocuccus pneumoniae 1 For 7 days in case of other organisms

TABLE 2

| | In vivo efficacy against systemic infections in mice | | | | | | | |
|---|---|---|---|---|---|---|---|---|
| | Streptococcus pyogenes A65 | | Streptococcus pneumoniae 1 | | Escherichia coli P5101 | | Pseudomonas aeruginosa 12 | |
| Compounds | po | iv | po | iv | po | iv | po | iv |
| 1a | 7.08 | 2.51 | 15.2 | 8.61 | 0.444 | 0.0355 | 1.85 | 0.516 |
| 2a | 11.2 | 4.26 | 21.5 | 15.8 | 0.413 | 0.0968 | 2.02 | 0.902 |
| 3a | 6.81 | ≈1.47 | 9.64 | 9.61 | 0.589 | 0.0986 | 2.01 | 1.05 |
| 4a | 7.43 | 2.46 | 7.27 | 3.64 | 0.456 | 0.0801 | 1.70 | 0.968 |
| A | 25.4 | >12.5 | 109 | 16.8 | 1.73 | 0.434 | 4.49 | 1.56 |
| B | 48.8 | >25 | 67.3 | 33.6 | 1.54 | 0.605 | 6.25 | ≈4.61 |

What is claimed is:

1. A 1,8-naphthyridine derivative of the formula

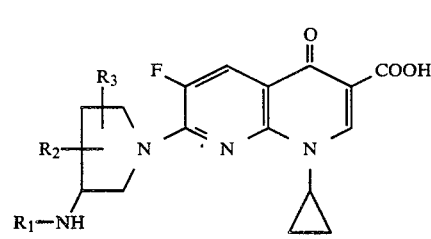

wherein $R_1$, $R_2$ and $R_3$ are the same or different and each is hydrogen or lower alkyl having 1 to 5 carbon atoms; or a pharmaceutically acceptable ester, or a pharmaceutically acceptable salt thereof.

2. A 1,8-naphthyridine derivative of the formula

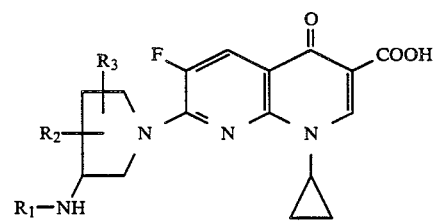

wherein $R_1$, $R_2$ and $R_3$ are the same or different and each is hydrogen or lower alkyl having 1 to 5 carbon atoms; or a pharmaceutically acceptable salt thereof.

3. A compound, salt or ester as claimed in claim 1, wherein $R_1$ is hydrogen or lower alkyl having 1 to 5 carbon atoms, and $R_2$ and $R_3$ are each hydrogen.

4. A compound, salt or ester as claimed in claim 1, wherein $R_2$ is lower alkyl having 1 to 5 carbon atoms, and $R_1$ and $R_3$ are hydrogen or lower alkyl having 1 to 5 carbon atoms.

5. A compound, salt or ester as claimed in claim 1, wherein $R_1$ is hydrogen, methyl or ethyl, and $R_2$ and $R_3$ are each hydrogen.

6. An alkyl, which has 1 to 5 carbon atoms, ester of 1,8-naphthyridine derivative of the formula

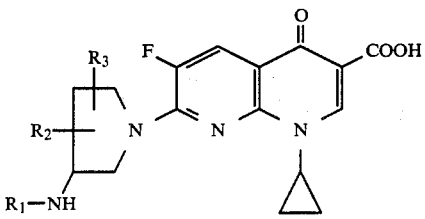

wherein $R_1$, $R_2$ and $R_3$ are the same or different and each is hydrogen or lower alkyl having 1 to 5 carbon atoms; or a pharmaceutically acceptable salt thereof.

7. A compound, salt or ester as claimed in claim 1, wherein $R_1$ is hydrogen, methyl or ethyl, $R_2$ is methyl or ethyl, and $R_3$ is hydrogen, methyl or ethyl.

8. 7-(3-Amino-1-pyrrolidinyl)-1-cyclopropyl-6-fluoro-1,4-dihydro-4-oxo-1,8-naphthyridine-3-carboxylic acid or a pharmaceutically acceptable acid addition salt thereof.

9. 1-Cyclopropyl-6-fluoro-7-(3-methylamino-1-pyrrolidinyl)-1,4-dihydro-4-oxo-1,8-naphthyridine-3-carboxylic acid or a pharmaceutically acceptable acid addition salt thereof.

10. 7-(3-Amino-4-methyl-1-pyrrolidinyl)-1-cyclopropyl-6-fluoro-1,4-dihydro-4-oxo-1,8-naphthyridine-3-carboxylic acid or a pharmaceutically acceptale acid addition salt thereof.

11. 7-(3-Amino-3-methyl-1-pyrrolidinyl)-1-cyclopropyl)-6-fluoro-1,4-dihydro-4-oxo-1,8-naphthyridine-3-carboxylic acid or a pharmaceutically acceptable acid addition salt thereof.

12. An antibacterial composition comprising as an active ingredient an antibacterially effective amount of a compound or ester or salt thereof as defined in claim 1 and a pharmaceutically acceptable carrier.

13. An antibacterial composition comprising as an active ingredient an antibacterially effective amount of a compound or ester or salt thereof as defined in claim 5 and a pharmaceutically acceptable carrier.

14. An antibacterial composition comprising as an active ingredient an antibacterially effective amount of a compound or ester or salt thereof as defined in claim 7 and a pharmaceutically acceptable carrier.

15. A method for treatment of a bacterial infectious disease which comprises administering to a warm-blooded animal an antibacterially effective amount of a compound or ester or salt thereof as defined in claim 1.

* * * * *

UNITED STATES PATENT AND TRADEMARK OFFICE
CERTIFICATE OF CORRECTION

PATENT NO. : 4,649,144
DATED : March 10, 1987
INVENTOR(S) : JUN-ICHI MATSUMOTO, TERUYUKI MIYAMOTO, HITOSHI UNO and SHINICHI NAKAMURA It is certified that error appears in the above-identified patent and that said Letters Patent is hereby corrected as shown below:

Column 8, line 26, change "reactin" to --reaction--.

Column 9, line 40, change "to" to --no--.

Column 10, line 1, change "In" to --in--.

UNITED STATES PATENT AND TRADEMARK OFFICE
CERTIFICATE OF CORRECTION

PATENT NO. : 4,649,144                             Page 2 of 5

DATED : March 10, 1987

INVENTOR(S) : JUN-ICHI MATSUMOTO, TERUYUKI MIYAMOTO, HITOSHI UNO and SHINICHI NAKAMURA It is certified that error appears in the above-identified patent and that said Letters Patent is hereby corrected as shown below:

Spanning columns 19 and 20, the reaction scheme depicted beginning at line 10, correct to read as follows:

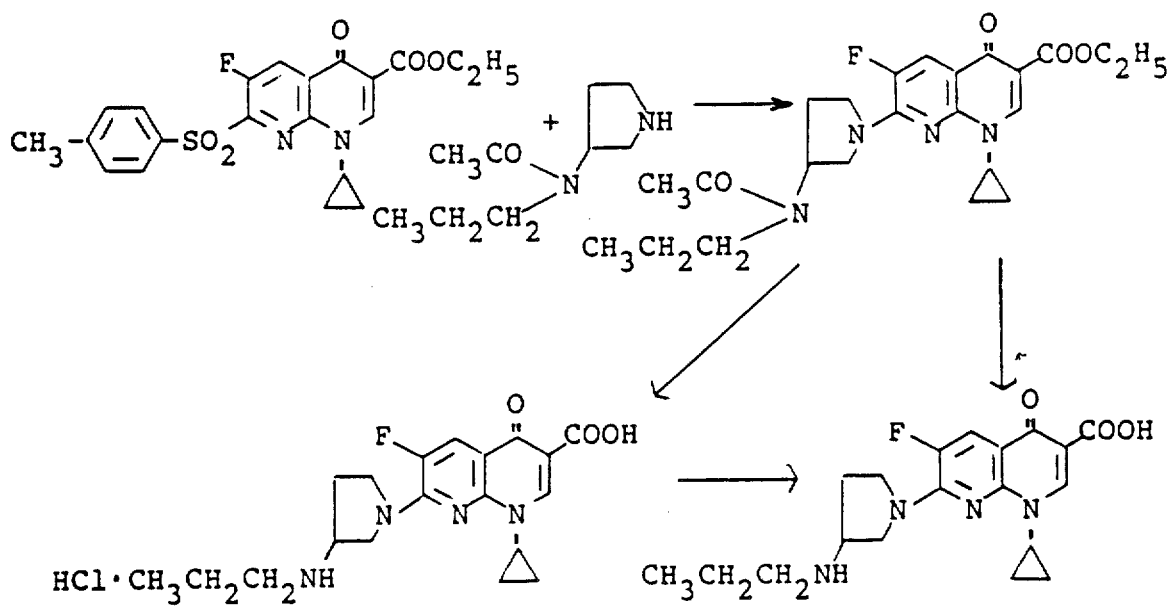

Column 21, line 50, change "dihydro-4oxo-1,8-" to

--dihydro-4-oxo-1,8- --.

UNITED STATES PATENT AND TRADEMARK OFFICE
CERTIFICATE OF CORRECTION

PATENT NO. : 4,649,144

DATED : March 10, 1987

INVENTOR(S) : JUN-ICHI MATSUMOTO, TERUYUKI MIYAMOTO, HITOSHI UNO and SHINICHI NAKAMURA It is certified that error appears in the above-identified patent and that said Letters Patent is hereby corrected as shown below:

Column 22, lines 50 to 55, correct the formula as follows:

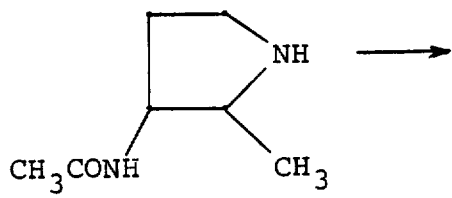

Column 24, lines 3 to 9, correct the formula as follows:

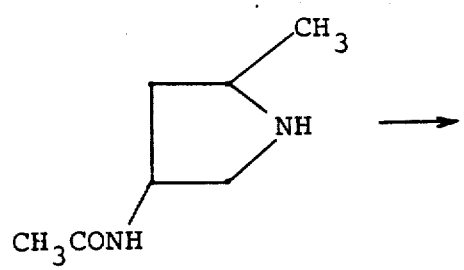

Column 28, line 68, change "-CH$_2$CH$_3$" to -- -CH$_2$CH$_3$--.

Column 31, line 9, change "ssubstitution" to --substition--;

line 55, change "ethanolisopropyl" to --ethanol-isopropyl--.

UNITED STATES PATENT AND TRADEMARK OFFICE
CERTIFICATE OF CORRECTION

PATENT NO.  :   4,649,144

DATED       :   March 10, 1987

INVENTOR(S) :   JUN-ICHI MATSUMOTO, TERUYUKI MIYAMOTO,
                HITOSHI UNO and SHINICHI NAKAMURA It is certified that error appears in the above-identified patent and that said Letters Patent is hereby corrected as shown below:

Column 32, line 42, change "ethoxycarbonylethyl-" to --ethoxycarbonylethyl)- --;

line 43, change ")amino]" to --amino]--.

Column 34, line 53, change "a" to --an--.

Column 36, line 16, change "1,8naphthyridine" to --1,8-naphthyridine--.

Column 38, line 18, change "comonents" to --components--;

line 68, change "29" to --29--.

Column 39, line 43, delete "Infec-";

line 44, change "tion:" to --Infection:--;

line 66, delete "For";

line 67, before "7" insert --For--.

UNITED STATES PATENT AND TRADEMARK OFFICE
CERTIFICATE OF CORRECTION

PATENT NO. : 4,649,144

DATED : March 10, 1987

INVENTOR(S) : JUN-ICHI MATSUMOTO, TERUYUKI MIYAMOTO, HITOSHI UNO and SHINICHI NAKAMURA It is certified that error appears in the above-identified patent and that said Letters Patent is hereby corrected as shown below:

Column 42, line 12, change "propyl)-6-" to --propyl-6- --.

Signed and Sealed this

Twenty-ninth Day of September, 1987

Attest:

DONALD J. QUIGG

Attesting Officer

Commissioner of Patents and Trademarks